(12) United States Patent
Fancelli et al.

(10) Patent No.: US 6,414,013 B1
(45) Date of Patent: Jul. 2, 2002

(54) THIOPHENE COMPOUNDS, PROCESS FOR PREPARING THE SAME, AND PHARMACEUTICAL COMPOSITIONS CONTAINING THE SAME BACKGROUND OF THE INVENTION

(75) Inventors: Daniele Fancelli, Milan; Paolo Pevarello, Pavia; Mario Varasi, Milan, all of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/596,550

(22) Filed: Jun. 19, 2000

(51) Int. Cl.$^7$ .................. A61K 31/38; C07D 333/02
(52) U.S. Cl. .................. 514/438; 514/445; 514/447; 549/29; 549/68; 549/70; 549/72; 549/74; 549/76
(58) Field of Search ................. 514/438, 445, 514/447; 549/29, 68, 70, 72, 74, 76

(56) References Cited

U.S. PATENT DOCUMENTS 3,963,750 A * 6/1976 Goudie et al. ........... 260/332.2

FOREIGN PATENT DOCUMENTS

| DE | 28 18 101 | 11/1978 |
| DE | 240 891 | 4/1985 |
| EP | 0 004 931 | 10/1979 |
| WO | WO 93/03040 | 2/1993 |
| WO | 9303040 | * 2/1993 |
| WO | WO 98/52558 | 11/1998 |
| WO | WO 98/52559 | 11/1998 |

OTHER PUBLICATIONS

Sauter et al. in Monatsh. Chem. 107/3,669–73(1976);"New Derivatives of thjiophene . . . ". also citedas HCAPLUS 1976:523697.*
U.S. application No. 09/807,962, Pending, filed Apr. 26, 2001.
U.S. application No. 09/769441, Pending, filed Jan. 26, 2001.
U.S. application No. 09/5996550, Pending, Jun. 19, 2000.

Brian Iddon et al., "Azoles. Part 7 A Convenient Synthesis of Thieno[2,3–d]imidazoles," *J. Chem. Soc. Perkin Trans.*, vol. 7, 1987, pp. 1457–1463, Xp001057768.
R. Pech, et al., "On–thirno–Compounds. Part 15. reaction of 2–aminothiophenes with Bismethylthiomethylene Derivatives," *Pharmazie*, vol. 48, No. 4, 1993, pp. 247–159. Xp001061686.

* cited by examiner

Primary Examiner—Mukund J. Shah
Assistant Examiner—Sudhaker B. Patel
(74) Attorney, Agent, or Firm—Oblon, Spivak, McClelland, Maier & Neustadt, P.C.

(57) ABSTRACT

Compounds which are 3-aminocarbonyl-2-carboxamido-thiophene derivatives of formula (I):

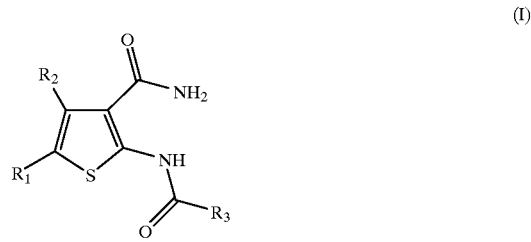

wherein $R_1$ and $R_2$ are, independently from each other, hydrogen, halogen or an optionally substituted group selected from aryl, straight or branched $C_1$–$C_6$ alkyl or aryl $C_1$–$C_6$ alkyl; or, taken together with the thiophene bond to which they are linked, $R_1$ and $R_2$ form a —$(CH_2)_m$—$(NR_4)_n$—$(CH_2)_p$— group wherein m and p are, each independently, an integer form 1 to 3, n is 0 or 1 and m+n+p is an integer from 3 to 5; and $R_4$ is hydrogen or an optionally substituted straight or branched $C_1$–$C_6$ alkyl group; $R_3$ is a group, optionally further substituted, selected from: i) straight or branched $C_1$–$C_8$ alkyl, $C_2$–$C_6$ alkenyl, $C_2$–$C_6$ alkynyl or $C_2$–$C_6$ alkylcarbonyl; ii) aryl; iii) 3 to 7 membered carbocycle; iv) 5 to 7 membered heterocycle with from 1 to 3 heteroatoms selected from nitrogen, oxygen and sulphur; or a pharmaceutically acceptable salt thereof; are useful in the treatment of diseases associated with an altered protein kinase activity such as cancer, Alzheimer's disease, viral infections, auto-immune diseases and neurodegenerative disorders.

45 Claims, No Drawings

THIOPHENE COMPOUNDS, PROCESS FOR PREPARING THE SAME, AND PHARMACEUTICAL COMPOSITIONS CONTAINING THE SAME BACKGROUND OF THE INVENTION

BACKGROUND OF THE INVENTION

1. Field of the Invention

The present invention relates to thiophene derivatives active as kinase inhibitors and, more in particular, it relates to 3-aminocarbonyl-2-carboxamido-thiophene derivatives, to a process for their preparation, to pharmaceutical compositions comprising them and to their use as therapeutic agents, particularly in the treatment of diseases linked to disregulated protein kinases.

2. Description of the Background

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neurofibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999,3, 459–465.

SUMMARY OF THE INVENTION

It is an object of the invention to provide compounds which are useful in therapy as agents against a host of diseases caused by a disregulated protein kinase activity.

It is another object to provide compounds which are endowed with multiple protein kinase inhibiting activity.

The present inventors have now discovered that 3-aminocarbonyl-2-carboxamido-thiophene derivatives are endowed with multiple protein kinase inhibiting activity and are thus useful in therapy in the treatment of diseases associated with disregulated protein kinases.

More specifically, the 3-aminocarbonyl-2-carboxamido-thiophene derivatives of this invention are useful in the treatment of a variety of cancers including, but not limited to: carcinoma such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Due to the key role of PKs in the regulation of cellular proliferation, these 3-aminocarbonyl-2-carboxamidothiophenes are also useful in the treatment of a variety of cell proliferative disorders such as, for instance, benign prostate hyperplasia, familial adenomatosis, polyposis, neurofibromatosis, psoriasis, vascular smooth cell proliferation associated with atherosclerosis, pulmonary fibrosis, arthritis glomerulonephritis and post-surgical stenosis and restenosis.

The compounds of the invention can be useful in the treatment of Alzheimer's disease, as suggested by the fact that cdk5 is involved in the phosphorylation of tau protein (J. Biochem., 117, 741–749, 1995).

The compounds of this invention, as modulators of apoptosis, may also be useful in the treatment of cancer, viral infections, prevention of AIDS development in HIV-infected individuals, autoimmune diseases and neurodegenerative disorders.

The compounds of this invention may be useful in inhibiting tumor angiogenesis and metastasis.

The compounds of this invention may also act as inhibitors of other protein kinases, e.g. protein kinase C in different isoforms, her2, raf1, MEK1, MAPK, EGF-R, PDGF-R, FGF-R, IGF-R, PI-3K, weel kinase, Src, Abl, Akt, ILK, PAK, CDKs/Cyclins, Chk, Plk, Nek, cdc7, auroral, aurora2 and thus be effective in the tretment of diseases associated with other protein kinases.

Accordingly, the present invention provides a method for treating diseases caused by and/or associated with an altered protein kinase activity, by administering to a mammal in need thereof an effective amount of a 3-aminocarbonyl-2-carboxamido-thiophene derivative represented by formula (I):

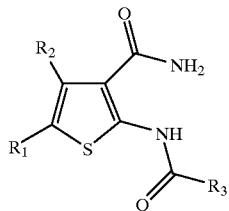

wherein $R_1$ and $R_2$ are, independently from each other, hydrogen, halogen or an optionally substituted group selected from aryl, straight or branched $C_1$–$C_6$ alkyl or aryl $C_1$–$C_6$ alkyl; or, taken together with the thiophene bond to which they are linked, $R_1$ and $R_2$ form a —$(CH_2)_m$—$(NR_4)_n$—$(CH_2)_p$— group wherein m and p are, each independently, an integer form 1 to 3, n is 0 or 1 and m+n+p is an integer from 3 to 5; and $R_4$ is hydrogen or an optionally substituted straight or branched $C_1$–$C_6$ alkyl group;

$R_3$ is a group, optionally further substituted, selected from:
 i) straight or branched $C_1$–$C_8$ alkyl, $C_2$–$C_6$ alkenyl, $C_2$–$C_6$ alkynyl or $C_2$–$C_6$ alkylcarbonyl;
 ii) aryl;
 iii) 3 to 7 membered carbocycle;
 iv) 5 to 7 membered heterocycle with from 1 to 3 heteroatoms selected from nitrogen, oxygen and sulphur;

or a pharmaceutically acceptable salt thereof.

In a preferred embodiment of the method described above, the disease caused by an altered protein kinase activity is selected from the group consisting of cancer, cell proliferative disorders, Alzheimer's disease, viral infections, auto-immune diseases and neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderoma pigmentosum, keratoxanthoma, thyroid follicular cancer and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

In addition, the method object of the present invention, also provides tumor angiogenesis and metastasis inhibition. Several 3-aminocarbonyl-2-carboxamido-thophene derivatives are known in the art, mostly as herbicides or synthetic intermediates and only few as therapeutic agents, particularly as anti-inflammatory agents.

See, for a general reference, Chemical Abstracts 108 (1988):112332; 85(1976):123697; 112(1990):118758; DE-A-4039734 and FR-A-2035767.

The international patent application WO 98/54116 in the name of Cadus Pharmaceutical Co. discloses thiophene derivatives possessing antitumor activity.

The present invention thus provides a 3-aminocarbonyl-2-carboxamido-thiophene derivative represented by formula (I):

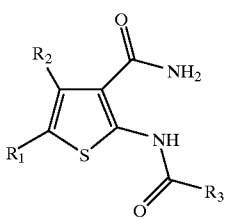

wherein
R$_1$ and R$_2$ are, independently from each other, hydrogen, halogen or an optionally substituted group selected from aryl, straight or branched C$_1$–C$_6$ alkyl or aryl C$_1$–C$_6$ alkyl;
or, taken together with the thiophene bond to which they are linked, R$_1$ and R$_2$ form a —(CH$_2$)$_m$—(NR$_4$)$_n$—(CH$_2$)$_p$— group wherein m and p are, each independently, an integer form 1 to 3, n is 0 or 1 and m+n+p is an integer from 3 to 5; and
R$_4$ is hydrogen or an optionally substituted straight or branched C$_1$–C$_6$ alkyl group;
R$_3$ is a group, optionally further substituted, selected from:
  i) straight or branched C$_1$–C$_8$ alkyl, C$_2$–C$_6$ alkenyl, C$_2$–C$_6$ alkynyl or C$_2$–C$_6$ alkylcarbonyl;
  ii) aryl;
  iii) 3 to 7 membered carbocycle;
  iv) 5 to 7 membered heterocycle with from 1 to 3 heteroatoms selected from nitrogen, oxygen and sulphur;
or a pharmaceutically acceptable salt thereof, provided that:
  a) when R$_1$ is phenyl and R$_2$ is hydrogen, then R$_3$ is other than phenyl or methyl;
  b) when R$_1$ and R$_2$ are both methyl, then R$_3$ is other than p-methoxyphenyl;
  c) when R$_1$ and R$_2$ together form a —(CH$_2$)$_4$— group, then R$_3$ is other than C$_1$–C$_4$ alkyl optionally substituted by halogen atoms; dimethylaminomethyl; diethylaminoethyl; phenyl optionally substituted by chlorine, methoxy, nitro or amino; and 2-(N-piperidino)ethyl;
  d) when R$_1$ and R$_2$ together form a —(CH$_2$)$_m$—(NR$_4$)$_n$—(CH$_2$)$_p$— group wherein m is 2, n and p are 1 and R$_4$ is hydrogen or methyl, then R$_3$ is other than methyl.

The compounds of formula (I), object of the present invention may, have asymmetric carbon atoms and may therefore exist either as racemic admixtures or as individual optical isomers.

Accordingly, all the possible isomers and their admixtures and of both the metabolites and the pharmaceutically acceptable bio-precursors (otherwise referred to as pro-drugs) of the compounds of formula (I), as well as any therapeutic method of treatment comprising them, are also within the scope of the present invention.

As used herein, unless otherwise specified, with the term halogen atom we intend a chlorine, bromine, fluorine or iodine atom.

With the term straight or branched C$_1$–C$_8$ alkyl we intend a group such as, for instance, methyl, ethyl, n.propyl, isopropyl, n.butyl, isobutyl, sec-butyl, tert-butyl, n.pentyl, n.hexyl, n.heptyl, n.octyl and the like.

With the term straight or branched C$_2$–C$_6$ alkenyl group or C$_2$–C$_6$ alkynyl group we intend, for instance, vinyl, allyl, isopropenyl, 1-, 2- or 3-butenyl, isobutylenyl, ethynyl, 1- or 2-propynyl, butynyl and the like.

With the term 3 to 7 membered carbocycle we intend either a saturated or partially unsaturated cycloalkyl group such as, for instance, cyclopropyl, cyclobutyl, cyclopentyl, cyclopentenyl, cyclohexyl, cyclohexenyl or cycloheptyl as well as bridged cycloalkyl groups, e.g. norbornene. With the term aryl, either as such or as arylalkyl group, we intend a mono-, bi- or poly- either carbocyclic as well as heterocyclic hydrocarbon with from 1 to 4 ring moieties, either fused or linked to each other by single bonds, wherein at least one of the carbocyclic or heterocyclic rings is aromatic.

Not limiting examples of aryl groups are, for instance, phenyl, indanyl, biphenyl, α- or β-naphthyl, fluorenyl, 9,10-dihydroanthracenyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, tetrazolyl, tetrazolylphenyl, pyrrolidinyl-tetrazolyl, isoindolinyl-phenyl, quinolinyl, isoquinolinyl, 2,6-diphenyl-pyridyl, quinoxalinyl, pyrazinyl, phenyl-quinolinyl, benzofurazanyl, 1,2,3-triazolyl, 1-phenyl-1,2,3-triazolyl, and the like.

With the term 5 to 7 membered heterocycle, hence encompassing aromatic heterocycles also referred to as aryl groups, we further intend a saturated or partially unsaturated 5 to 7 membered carbocycle wherein one or more carbon atoms are replaced by heteroatoms such as nitrogen, oxygen and sulphur.

Examples of 5 to 7 membered heterocycles, optionally benzocondensed or further substituted, are 1,3-dioxolane, pyran, pyrrolidine, pyrroline, imidazolidine, pyrazolidine, pyrazoline, piperidine, piperazine, morpholine, tetrahydrofuran, azabicyclononane and the like.

According to the above meanings provided to the R$_1$, R$_2$ and R$_3$ substituents, any of the above groups may be further optionally substituted in any of the free positions by one or more groups, for instance 1 to 6 groups, selected from: halogen, nitro, oxo groups (=O), carboxy, cyano, alkyl, perfluorinated alkyl, alkenyl, alkynyl, cycloalkyl, aryl, heterocyclyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, aryloxy, alkylcarbonyloxy, arylcarbonyloxy, cycloalkenyloxy or alkylideneaminooxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulphonyl, arylsulphonyl, alkylsulphinyl, arylsulphinyl, arylsulphonyloxy, aminosulfonyl, alkylaminosulphonyl or dialkylaminosulphonyl. In their turn, whenever appropriate, each of the above substituents may be further substituted by one or more of the aforementioned groups.

Pharmaceutically acceptable salts of the compounds of formula (I) are the acid addition salts with inorganic or organic, e.g. nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

Preferred compounds of the invention of formula (I) are the compounds wherein $R_1$ and $R_2$ are selected, each independently, from hydrogen, $C_1$–$C_4$ alkyl or optionally substituted aryl or aryl $C_1$–$C_4$ alkyl groups and $R_3$ has the above reported meanings.

Another class of preferred compounds (I) of the invention are the compounds wherein $R_1$ and $R_2$ together form a —$(CH_2)_m$—$(NR_4)_n$—$(CH_2)_p$— group, n is 0 or 1, $R_4$ if present is $C_1$–$C_4$ alkyl, preferably methyl, m+n+p is 4 and $R_3$ has the above reported meanings.

Even more preferred compounds of the invention, within the above classes, are the compounds of formula (I) wherein $R_1$ is selected from isopropyl, phenyl, phenylmethyl or 1-phenylethyl and $R_2$ is hydrogen; or $R_1$ is hydrogen and $R_2$ is methyl or 4-fluorophenyl; or $R_1$ and $R_2$ are both methyl groups or form, together, a —$(CH_2)_4$— group or a —$CH_2$—$NR_4$—$(CH_2)_2$— group wherein $R_4$ is $C_1$–$C_4$ alkyl, preferably methyl, and $R_3$ has the above reported meanings.

All of the preferred compounds of the invention, whenever appropriate in the form of pharmaceutically acceptable salts, e.g. hydrobromide or hydrochloride salts, are herewith conveniently indicated and defined as products by process, that is as products of formula (I) which are obtainable, for instance through a defined process.

More in particular, specific preferred compounds (I) of the invention are the compounds which are obtainable, for instance through a combinatorial chemistry technique, by reacting each of the amino-thiophene derivatives of formula (II), as set forth in table I, with any one of the carboxylic acid derivatives of formula $R_3$—COOH (III), as set forth in table II.

TABLE I

Amino-thiophene derivatives of formula (II)

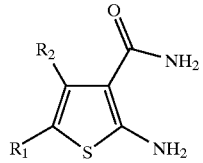

(II)

| $R_1$ | $R_2$ |
|---|---|
| Isopropyl | Hydrogen |
| Phenyl | Hydrogen |
| Phenylmethyl | Hydrogen |
| 1-phenylethyl | Hydrogen |
| Methyl | Methyl |
| Hydrogen | Methyl |
| Hydrogen | 4-fluorophenyl |
| —$(CH_2)_4$— | |
| —$CH_2$—$N(CH_3)$—$(CH_2)_2$— | |

TABLE II

Carboxylic acid derivatives of formula $R_3$—COOH (III)

| Entry | $R_3$—COOH |
|---|---|
| 1. | ACETIC |
| 2. | PROPIONIC |
| 3. | 2-BUTYNOIC |
| 4. | CYANOACETIC |
| 5. | CYCLOPROPANECARBOXYLIC |
| 6. | ISOBUTYRIC |
| 7. | 3,3-DIMETHYLACRYLIC |
| 8. | 2-KETOBUTYRIC |
| 9. | N,N-DIMETHYLGLYCINE |
| 10. | 3-CHLOROPROPIONIC |
| 11. | PYRROLE-2-CARBOXYLIC |
| 12. | 1-CYANOCYCLOPROPANECARBOXYLIC |
| 13. | PYRROLE-3-CARBOXYLIC |
| 14. | 4-PYRAZOLECARBOXYLIC |
| 15. | IMIDAZOL-4-CARBOXYLIC |
| 16. | CYCLOPENTANECARBOXYLIC |
| 17. | N-ACETYLGLYCINE |
| 18. | BENZOIC |
| 19. | PICOLINIC |
| 20. | NICOTINIC |
| 21. | ISONICOTINIC |
| 22. | 2-PYRAZINECARBOXYLIC |
| 23. | 1-METHYLPYRROLE-2-CARBOXYLIC |
| 24. | 3-METHYL-2-FUROIC |
| 25. | 5-METHYLISOXAZOLE-4-CARBOXYLIC |
| 26. | 3-METHYLISOXAZOLE-4-CARBOXYLIC |
| 27. | 5-METHYLISOXAZOLE-3-CARBOXYLIC |
| 28. | 3-AMINOPYRAZOLE-4-CARBOXYLIC |
| 29. | THIOPHENE-2-CARBOXYLIC |
| 30. | THIOPHENE-3-CARBOXYLIC |
| 31. | CYCLOPENTYLACETIC |
| 32. | DL-PYROGLUTAMIC |
| 33. | 1-(AMINOCARBONYL)-1-CYCLOPROPANECARBOXYLIC |
| 34. | N-ME-PRO-OH |
| 35. | 2-IMIDAZOLIDONE-4- |

TABLE II-continued

Carboxylic acid derivatives of formula R₃—COOH (III)

| Entry | R₃—COOH |
|---|---|
| 36. | N-ACETYL-DL-ALANINE |
| 37. | 3-UREIDOPROPIONIC |
| 38. | O-TOLUIC |
| 39. | M-TOLUIC |
| 40. | P-TOLUIC |
| 41. | PHENYLACETIC |
| 42. | SALICYLIC |
| 43. | 3-HYDROXYBENZOIC |
| 44. | 4-HYDROXYBENZOIC |
| 45. | UROCANIC |
| 46. | 2-METHYLPYRAZINE-5-CARBOXYLIC |
| 47. | 5-NORBORNENE-2-CARBOXYLIC |
| 48. | 2-FLUOROBENZOIC |
| 49. | 3-FLUOROBENZOIC |
| 50. | 4-FLUOROBENZOIC |
| 51. | 3,5-DIMETHYLISOXAZOLE-4-CARBOXYLIC |
| 52. | THIOPHENE-2-ACETIC |
| 53. | THIOPHENE-3-ACETIC |
| 54. | 3-CYCLOPENTYLPROPIONIC |
| 55. | CYCLOHEPTANECARBOXYLIC |
| 56. | 2,2-DIMETHYLHEXANOIC |
| 57. | ALPHA-(ISOPROPYLIDENEAMINOOXY)PROPIONIC |
| 58. | N,N-DIMETHYLSUCCINAMIC |
| 59. | PHENYLPROPIOLIC |
| 60. | N-CARBAMYL-DL-ALPHA-AMINO-N-BUTYRIC |
| 61. | 3-CYANOBENZOIC |
| 62. | 4-CYANOBENZOIC |
| 63. | N-METHYL-L-PROLINE MONOHYDRATE |
| 64. | TRANS-CINNAMIC |
| 65. | 3-(3-PYRIDYL)ACRYLIC |
| 66. | 3-(4-PYRIDYL)-ACRYLIC |
| 67. | 2,3-DIMETHYLBENZOIC |
| 68. | 2,4-DIMETHYLBENZOIC |
| 69. | 2,5-DIMETHYLBENZOIC |
| 70. | 2,6-DIMETHYLBENZOIC |
| 71. | 3,4-DIMETHYLBENZOIC |
| 72. | 3,5-DIMETHYLBENZOIC |
| 73. | 2-PHENYLPROPIONIC |
| 74. | HYDROCINNAMIC |
| 75. | O-TOLYLACETIC |
| 76. | M-TOLYLACETIC |
| 77. | P-TOLYLACETIC |
| 78. | 3-PYRIDINEPROPIONIC |
| 79. | O-ANISIC |
| 80. | 3-METHYLSALICYLIC |
| 81. | 4-METHYLSALICYLIC |
| 82. | 5-METHYLSALICYLIC |
| 83. | 3-METHOXYBENZOIC |
| 84. | 3-HYDROXY-4-METHYLBENZOIC |
| 85. | P-ANISIC |
| 86. | PHENOXYACETIC |
| 87. | 2-HYDROXYPHENYLACETIC |
| 88. | 3-HYDROXYPHENYLACETIC |
| 89. | 4-HYDROXYPHENYLACETIC |
| 90. | DL-MANDELIC |
| 91. | 3-HYDROXY-O-TOLUIC |
| 92. | ALPHA-FLUOROPHENYLACETIC |
| 93. | 2-FLUOROPHENYLACETIC |
| 94. | 3-FLUOROPHENYLACETIC |
| 95. | 4-FLUOROPHENYLACETIC |
| 96. | 3-(2-THIENYL)ACRYLIC |
| 97. | 3-(3-THIENYL)-ACRYLIC |
| 98. | 3-(2-THIENYL)PROPANOIC |
| 99. | CYCLOHEPTYLACETIC |
| 100. | 2-CHLOROBENZOIC |
| 101. | 3-CHLOROBENZOIC |
| 102. | 4-CHLOROBENZOIC |
| 103. | N-PROPYLMALEAMIC |
| 104. | N-ACETYL-DL-ALLYLGLYCINE |
| 105. | AC-DL-PRO-OH |
| 106. | 1-PIPERIDINEPROPIONIC |
| 107. | 2-CHLORONICOTINIC |
| 108. | 6-CHLORONICOTINIC |
| 109. | N-CARBAMOYLMALEAMIC |
| 110. | N-(ACETOACETYL)GLYCINE |
| 111. | N-ACETYL-DL-VALINE |
| 112. | N-CARBAMYL-DL-NORVALINE |
| 113. | N-CARBAMYL-DL-VALINE |
| 114. | DL-ALANYL-DL-ALANINE |
| 115. | INDOLE-2-CARBOXYLIC |
| 116. | INDOLE-3-CARBOXYLIC |
| 117. | INDOLE-5-CARBOXYLIC |
| 118. | INDOLE-4-CARBOXYLIC |
| 119. | INDOLE-6-CARBOXYLIC |
| 120. | BENZOFURAN-2-CARBOXYLIC |
| 121. | 5-BENZIMIDAZOLECARBOXYLIC |
| 122. | INDAZOLE-3-CARBOXYLIC |
| 123. | 1-PHENYL-1-CYCLOPROPANECARBOXYLIC |
| 124. | ALPHA-METHYLCINNAMIC |
| 125. | 4-IMIDAZOLEACETIC HYDROCHLORIDE |
| 126. | 6-CARBOXYPURINE |
| 127. | 2-ACETYLBENZOIC |
| 128. | 4-ACETYLBENZOIC |
| 129. | O-COUMARIC |
| 130. | 3-HYDROXYCINNAMIC |
| 131. | 4-HYDROXYCINNAMIC |
| 132. | P-COUMARIC |
| 133. | 4-ISOPROPYLBENZOIC |
| 134. | 2-(3,5-XYLYL)ACETIC |
| 135. | PHTHALAMIC |
| 136. | 3-DIMETHYLAMINOBENZOIC |
| 137. | 4-DIMETHYLAMINOBENZOIC |
| 138. | 2-DIMETHYLAMINOBENZOIC |
| 139. | PIPERONYLIC |
| 140. | ALPHA-FLUOROCINNAMIC |
| 141. | 3-METHOXY-4-METHYLBENZOIC |
| 142. | 4-HYDROXY-3,5-DIMETHYLBENZOIC |
| 143. | BENZYLOXYACETIC |
| 144. | 4-DIMETHYLAMINOBUTYRIC HYDROCHLORIDE |
| 145. | 3-METHOXYSALICYLIC |
| 146. | 4-METHOXYSALICYLIC |
| 147. | 5-METHOXYSALICYLIC |
| 148. | 3-HYDROXY-4-METHOXYBENZOIC |
| 149. | VANILLIC |
| 150. | 4-HYDROXYPHENOXYACETIC |
| 151. | 6-METHOXYSALICYLIC |
| 152. | N-(2-FUROYL)GLYCINE |
| 153. | BETA-MALEIMIDOPROPIONIC |
| 154. | 3,4-DIHYDRO-2,2-DIMETHYL-4-OXO-2H-PYRAN-6-CARBOXYLIC |
| 155. | 5-ACETYLTHIOPHENE-2-CARBOXYLIC |
| 156. | 1-ACETYLPIPERIDINE-4-CARBOXYLIC |
| 157. | 1-NAPHTHOIC |
| 158. | 2-NAPHTHOIC |
| 159. | 4-CHLOROSALICYLIC |
| 160. | 5-CHLOROSALICYLIC |
| 161. | 3-CHLORO-4-HYDROXYBENZOIC |
| 162. | 3-CHLOROSALICYLIC |
| 163. | AC-HYP-OH |
| 164. | QUINALDIC |
| 165. | QUINOLINE-3-CARBOXYLIC |
| 166. | QUINOLINE-4-CARBOXYLIC |
| 167. | 1-ISOQUINOLINECARBOXYLIC |
| 168. | QUINOLINE-6-CARBOXYLIC |
| 169. | QUINOLINE-8-CARBOXYLIC |
| 170. | 6-ACETAMIDOHEXANOIC |
| 171. | N-ACETYL-DL-LEUCINE |
| 172. | N,N-DI-N-PROPYL-L-ALANINE |
| 173. | NALPHA-ACETYL-L-ASPARAGINE |
| 174. | CINNOLINE-4-CARBOXYLIC |

TABLE II-continued

Carboxylic acid derivatives of formula R₃—COOH (III)

| Entry | R₃—COOH |
|---|---|
| 175. | 2-QUINOXALINECARBOXYLIC |
| 176. | 3-METHYLINDENE-2-CARBOXYLIC |
| 177. | INDOLE-3-ACETIC |
| 178. | 1-METHYLINDOLE-2-CARBOXYLIC |
| 179. | 5-METHYLINDOLE-2-CARBOXYLIC |
| 180. | 1-METHYLINDOLE-3-CARBOXYLIC |
| 181. | INDAZOLONE-4-CARBOXYLIC |
| 182. | 3-OXO-1-INDANCARBOXYLIC |
| 183. | 2-METHYL-1H-BENZIMIDAZOLE-5-CARBOXYLIC |
| 184. | 1,2,3,4-TETRAHYDRO-2-NAPHTHOIC |
| 185. | 2-INDANYLACETIC |
| 186. | 1-METHYL-4-IMIDAZOLE-ACETIC HYDROCHLORIDE |
| 187. | 5-HYDROXYINDOLE-2-CARBOXYLIC |
| 188. | ARECAIDINE HYDROCHLORIDE |
| 189. | 3-BENZOYLPROPIONIC |
| 190. | 4-METHOXYCINNAMIC |
| 191. | 2-METHOXYCINNAMIC |
| 192. | BENZO[B]THIOPHENE-2-CARBOXYLIC |
| 193. | 2-ISOPROPYL-2-PHENYLACETIC |
| 194. | N-ACETYLANTHRANILIC |
| 195. | 4-ACETAMIDOBENZOIC |
| 196. | HIPPURIC |
| 197. | 3-ACETAMIDOBENZOIC |
| 198. | N-CHLOROACETYL-DL-2-AMINO-N-BUTYRIC |
| 199. | 3,4-METHYLENEDIOXYPHENYLACETIC |
| 200. | NICOTINURIC |
| 201. | 4-ISOPROPOXYBENZOIC |
| 202. | 3-(DIETHYLAMINO)PROPIONIC HYDROCHLORIDE |
| 203. | 2,5-DIMETHOXYBENZOIC |
| 204. | 2,6-DIMETHOXYBENZOIC |
| 205. | 3,4-DIMETHOXYBENZOIC |
| 206. | 3,5-DIMETHOXYBENZOIC |
| 207. | 2-METHOXYPHENOXYACETIC |
| 208. | THYMINE-1-ACETIC |
| 209. | 3-(2-THENOYL)-PROPIONIC |
| 210. | 3-CHLORO-4-METHOXYBENZOIC |
| 211. | 5-CHLORO-2-METHOXYBENZOIC |
| 212. | 1-(2-CARBOXYPHENYL)PYRROLE |
| 213. | 4-(1H-PYRROL-1-YL)BENZOIC |
| 214. | 3-INDOLEPROPIONIC |
| 215. | 2-METHYL-3-INDOLEACETIC |
| 216. | 1-METHYL-3-INDOLEACETIC |
| 217. | 2-(TRIFLUOROMETHYL)BENZOIC |
| 218. | 3-(TRIFLUOROMETHYL)BENZOIC |
| 219. | 4-(TRIFLUOROMETHYL)BENZOIC |
| 220. | CHROMONE-2-CARBOXYLIC |
| 221. | CHROMONE-3-CARBOXYLIC |
| 222. | 3-HYDROXY-2-QUINOXALINECARBOXYLIC |
| 223. | 2-BENZIMIDAZOLEPROPIONIC |
| 224. | 1-PHENYL-1-CYCLOPENTANECARBOXYLIC |
| 225. | 2,3-DICHLOROBENZOIC |
| 226. | 2,4-DICHLOROBENZOIC |
| 227. | 2,5-DICHLOROBENZOIC |
| 228. | 2,6-DICHLOROBENZOIC |
| 229. | 3,4-DICHLOROBENZOIC |
| 230. | 3,5-DICHLOROBENZOIC |
| 231. | 5-METHOXYINDOLE-2-CARBOXYLIC |
| 232. | 5-HYDROXYINDOLE-3-ACETIC |
| 233. | 4-OXO-4-PHENYLAMINO-2-BUTENOIC |
| 234. | 4-(DIMETHYLAMINO)CINNAMIC |
| 235. | 3,4-METHYLENEDIOXYCINNAMIC |
| 236. | 7-METHOXYBENZOFURAN-2-CARBOXYLIC |
| 237. | 4-BENZOYLBUTYRIC |
| 238. | BENZO[B]THIOPHENE-3-ACETIC |
| 239. | 5-FLUOROINDOLE-3-ACETIC |
| 240. | N-BENZOYL-BETA-ALANINE |
| 241. | AC-DL-PHG-OH |
| 242. | BZ-ALA-OH |
| 243. | N-METHYLHIPPURIC |
| 244. | O-HYDROXYHIPPURIC |
| 245. | FA-GLY-OH |
| 246. | 5-CHLOROINDOLE-2-CARBOXYLIC |
| 247. | (3,5-DIMETHOXYPHENYL)ACETIC |
| 248. | 3,5-DIMETHOXY-4-METHYLBENZOIC |
| 249. | (2,4-DIMETHOXY-PHENYL)-ACETIC |
| 250. | N-ACETYL-L-HISTIDINE |
| 251. | 5-(2-THIENOYL)BUTYRIC |
| 252. | 4-(METHYLSULFONYL)BENZOIC |
| 253. | PHENYLSULPHONYLACETIC |
| 254. | 3-(METHYLSULFONYL)BENZOIC |
| 255. | 2-(METHYLSULFONYL)BENZOIC |
| 256. | 4-CARBOXYBENZENESULFONAMIDE |
| 257. | 5-METHYL-1-PHENYLPYRAZOLE-4-CARBOXYLIC |
| 258. | 5-METHYL-3-PHENYLISOXAZOLE-4-CARBOXYLIC |
| 259. | 2-HYDROXY-5-(1H-PYRROL-1-YL)BENZOIC |
| 260. | 4-METHYL-2-PHENYL-1,2,3-TRIAZOLE-5-CARBOXYLIC |
| 261. | INDOLE-3-BUTYRIC |
| 262. | AC-DL-PHE-OH |
| 263. | 2,3-DIMETHOXYCINNAMIC |
| 264. | 2,5-DIMETHOXYCINNAMIC |
| 265. | 3,4-DIMETHOXYCINNAMIC |
| 266. | 3,5-DIMETHOXYCINNAMIC |
| 267. | 2,4-DIMETHOXYCINNAMIC |
| 268. | 4-CHLOROINDOLE-3-ACETIC |
| 269. | 3-(3,4-DIMETHOXYPHENYL)PROPIONIC |
| 270. | 9-FLUORENECARBOXYLIC |
| 271. | 6-CHLORO(2H)-1-BENZOPYRAN-3-CARBOXYLIC |
| 272. | EPSILON-MALEIMIDOCAPROIC |
| 273. | 2,3,4-TRIMETHOXYBENZOIC |
| 274. | 2,4,5-TRIMETHOXYBENZOIC |
| 275. | 3,4,5-TRIMETHOXYBENZOIC |
| 276. | 2,4,6-TRIMETHOXYBENZOIC |
| 277. | 3-CHLOROBENZO[B]THIOPHENE-2-CARBOXYLIC |
| 278. | 3-(PHENYLSULFONYL)PROPIONIC |
| 279. | 4-TOLUENESULFONYLACETIC |
| 280. | 4-METHYLSULFONYLPHENYLACETIC |
| 281. | D-DESTHIOBIOTIN |
| 282. | 3-PHTHALIMIDO-PROPIONIC |
| 283. | 5-METHOXY-2-METHYL-3-INDOLEACETIC |
| 284. | 5-METHOXY-1-INDANONE-3-ACETIC |
| 285. | 5-(4-CHLOROPHENYL)-2-FUROIC |
| 286. | 6-CHLOROKYNURENIC |
| 287. | N-(4-CHLOROPHENYL)MALEAMIC |
| 288. | N-P-TOSYLGLYCINE |
| 289. | 4,6-DICHLOROINDOLE-2-CARBOXYLIC |
| 290. | N-(1-NAPHTHYL)MALEAMIC |
| 291. | 3-IODOBENZOIC |
| 292. | 4-IODOBENZOIC |
| 293. | N-M-TOLYLPHTHALAMIC |
| 294. | 3-ACETAMINO-6-BROMOBENZOIC |

TABLE II-continued

Carboxylic acid derivatives of formula R₃—COOH (III)

| Entry | R₃—COOH |
|---|---|
| 295. | 2-ACETAMIDO-5-BROMOBENZOIC |
| 296. | BZ-HIS-OH |
| 297. | 2-IODOPHENYLACETIC |
| 298. | 4-IODOPHENYLACETIC |
| 299. | 8-(3-CARBOXYPROPYL)-1,3-DIMETHYLXANTHINE |
| 300. | 7-BROMOKYNURENIC |
| 301. | N-BENZOYL-DL-PHENYLALANINE |

More specifically, herewith provided are novel compounds of formula (I) which are obtainable through a process comprising reacting the 2-amino-thiophene derivative of formula (II)

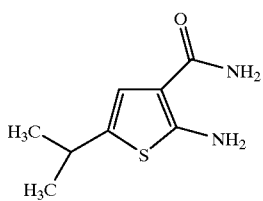
(II)

with each one of the carboxylic acids listed in table II.

Also provided are novel compounds of formula (I) which are obtainable through a process comprising reacting the 2-amino-thiophene derivative of formula (II)

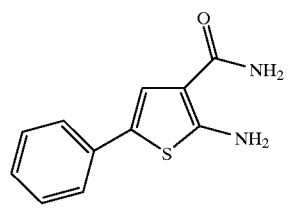
(II)

with each one of the carboxylic acids listed in table II other than benzoic or acetic acid.

Also provided are novel compounds of formula (I) which are obtainable through a process comprising reacting the 2-amino-thiophene derivative of formula (II)

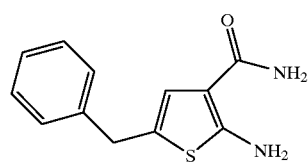
(II)

with each one of the carboxylic acids of table II.

Also provided are novel compounds of formula (I) which are obtainable through a process comprising reacting the 2-amino-thiophene derivative of formula (II)

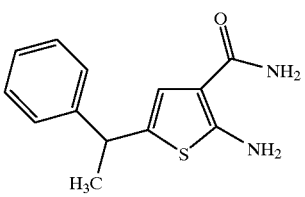
(II)

with each one of the carboxylic acids of table II.

Also provided are novel compounds of formula (I) which are obtainable through a process comprising reacting the 2-amino-thiophene derivative of formula (II)

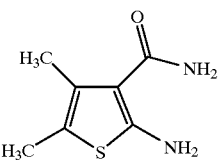
(II)

with each one of the carboxylic acids of table II other than p-anisic acid.

Also provided are novel compounds of formula (I) which are obtainable through a process comprising reacting the 2-amino-thiophene derivative of formula (II)

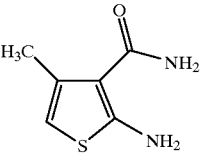
(II)

with each one of the carboxylic acids of table II.

Also provided are novel compounds of formula (I) which are obtainable through a process comprising reacting the 2-amino-thiophene derivative of formula (II)

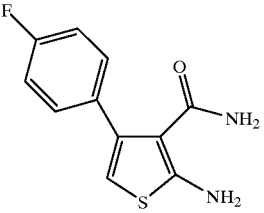
(II)

with each one of the carboxylic acids of table II.

Also provided are novel compounds of formula (I) which are obtainable through a process comprising reacting the 2-amino-thiophene derivative of formula (II)

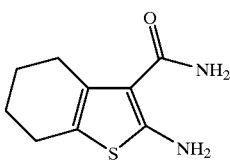

(II)

with each one of the carboxylic acids of table II provided that $R_3$ is other than methyl, ethyl, dimethylaminomethyl, diethylaminoethyl, phenyl, 4-chlorophenyl, 4-methoxyphenyl or 2-(N-piperidino)ethyl.

Also provided are novel compounds of formula (I) which are obtainable through a process comprising reacting the 2-amino-thiophene derivative of formula (II)

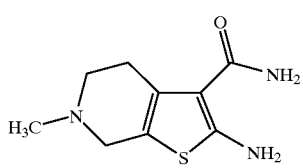

(II)

with each one of the carboxylic acids of table II other than acetic.

As set forth above, it is a further object of the present invention a process for preparing the 3-aminocarbonyl-2-carboxamido-thiophene derivatives of formula (I).

The compounds of formula (I) and the salts thereof may be obtained, for instance, by a process comprising reacting a compound of formula (II)

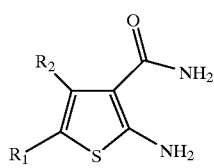

(II)

with a compound of formula (III)

$R_3$—COX    (III)

wherein $R_1$, $R_2$ and $R_3$ are as defined above and X is hydroxy or a suitable leaving group; and, if desired, converting a 2-aminocarbonyl-3-carboxamido-thiophene derivative of formula (I) into another such derivative of formula (I), and/or into a salt thereof.

Examples of specific leaving groups X within the compounds of formula (III) are halogen atoms.

Preferably, X is hydroxy, chlorine or bromine.

It is clear to the person skilled in the art that if a compound of formula (I), prepared according to the above process, is obtained as an admixture of isomers, their separation into the single isomers of formula (I) carried out according to conventional techniques, is still within the scope of the present invention.

Likewise, the conversion into the free compound (I) of a corresponding salt thereof, according to well-known procedures in the art, is still within the scope of the invention.

The above process is an analogy process which can be carried out according to well known methods.

The reaction between a compound of formula (II) and a carboxylic of formula (III) wherein X is hydroxy can be carried out in the presence of a coupling agent such as, for instance, carbodiimide, i.e. 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about —10° C. to reflux for a suitable time, i.e. from about 30 min. to about 96 hours. The said reaction is optionally carried out in the presence of a suitable catalyst, for instance 4-dimethylaminopyridine, or in the presence of a further coupling reagent such as N-hydroxybenzotriazole.

The reaction between a compound of formula (II) and a compound of formula (III) can be also carried out, for example, through a mixed anhydride method, by using an alkyl chloroformate, such as ethyl, iso-butyl, or iso-propyl chloroformate, in the presence of a tertiary base, such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

The reaction between a compound of formula (II) and a carboxylic derivative of formula (III) wherein X is a suitable leaving group can be carried out in the presence of a tertiary base, such as triethylamine, N,N-diisopropylethylamine or pyridine, in a suitable solvent, such as toluene, dichloromethane, chloroform, diethyl ether, tetrahydrofuran, acetonitrile, or N,N-dimethylformamide, at a temperature ranging from about −10° C. to reflux.

Also the optional conversion of a compound of formula (I) into another compound of formula (I) can be carried out according to known methods.

As an example, an alkylthio or an arylthio group may be converted into the corresponding alkylsulfonyl and arylsulfonyl group by reaction, for example, with m-chloroperbenzoic in a suitable solvent such as dichloromethane or chloroform, at a temperature varying between about −5° C. and room temperature.

The optional salification of a compound of formula (I) or the conversion of its salt into the free compound, as well as the separation of a mixture of isomers into the single isomers, may all be carried out by conventional methods.

The compounds of formula (II) and (III) according to the process object of the present invention are known compounds or can be obtained according to known methods. For example, a compound of formula (II) wherein $R_1$ and $R_2$ are as defined above can be obtained from a compound of formula (IV)

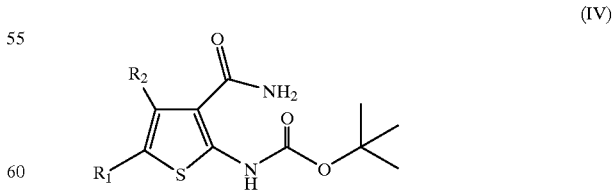

(IV)

by treatment with an organic or mineral acid, for instance trifluoroacetic or hydrochloric acid, in a suitable solvent such as tetrahydrofuran, dichloromethane, at a temperature varying between −10° C. and reflux, for a time ranging from about 1 hour to about 24 hours.

A compound of formula (IV), in its turn, can be obtained by treating the corresponding carboxylic derivative of formula (V), wherein $R_1$ and $R_2$ are as defined above and Z is chlorine, methoxy, or ethoxy

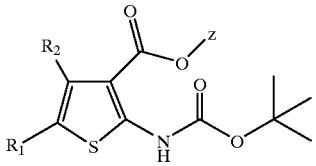

(V)

with ammonia in a suitable solvent such as dioxane, dichloromethane or acetonitril. Also the optional conversion of a compound of formula (V) into another compound of formula (V) can be carried out according to known methods.

A compound of formula (V) can be obtained by treating the corresponding amino derivative (VI), wherein $R_1$ and $R_2$ are as defined above and W is methoxy, or ethoxy

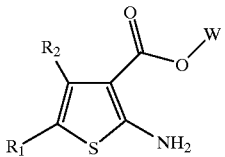

(VI)

with di-t-butyl-dicarbonate in a suitable solvent such as dioxane, dichloromethane or acetonitrile, in the presence of a proton scavenger such as triethylamine or diisopropylethylamine at a temperature ranging from 0° C. to reflux.

Compounds of formula (VI) are either commercially available compounds or can be prepared from commercially available precursors according to known methodologies, for instance as described in Chem. Ber. 1966, 99, 94; and J. Med. Chem. 1981, 24, 878.

A compound of formula (III) wherein X is a leaving group as defined above can be obtained according to conventional techniques from the corresponding carboxylic acids of formula (III) wherein X is hydroxy.

When preparing the compounds of formula (I) according to the process object of the present invention, optional functional groups within both the starting materials or the intermediates thereof, which could give rise to unwanted side reactions, need to be properly protected according to conventional techniques.

Likewise, the conversion of these latter into the free deprotected compounds may be carried out according to known procedures.

The compounds of formula (I) of the invention were prepared according to combinatorial chemistry techniques widely known in the art, by accomplishing the aforementioned condensation reactions between the compounds of formula (II) with those of formula (III) in a serial manner.

As an example, the compounds of the invention may be prepared by reacting each of the amino derivatives of formula (II) wherein $R_1$ and $R_2$ are as above defined, for instance as reported in table I, with each of the carboxylic acids of formula (III), as per table II, wherein $R_3$ is as above defined, or derivatives thereof wherein X is a suitable leaving group.

Pharmacology

The compounds of formula (I), are active as protein kinase inhibitors as they gave positive results when tested according to the following procedures.

The compounds of formula (I) are therefore useful to restrict the unregulated proliferation of tumor cells, hence in therapy in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative protein kinase inhibitors and the potency of selected compounds was determined through a method of assay based on the use of the MultiScreen-PH 96 well plate (Millipore), in which a phosphocellulose filter paper was placed at each well bottom allowing binding of positive charged substrate after a washing/filtration step.

When a radioactivity labelled phosphate moiety was transferred by the kinase to the filter-bound histone, light emitted was measured in a scintillation counter. As an example, not limiting the scope of the invention, the inhibition assay of protein kinase activity was performed according to the following protocol:

Kinase reaction: 1.5 μM histone H1 substrate, 25 μM ATP (0.5 uCi $P^{33}$g-ATP), 100 ng Cyclin A/cdk2 complex, 10 μM inhibitor in a final volume of 100 μl buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 μl EDTA 120 mM.

Capture: 100 μl were transferred from each well to MultiScreen plate, to allow substrate binding to phosphocellulose filter. Plates were then washed 3 times with 150 μl/well PBS $Ca^{++}/Mg^{++}$ free and filtered by MultiScreen filtration system.

Detection: filters were allowed to dry at 37° C., then 100 μl/well scintillant were added and $^{33}P$ labelled histone H1 was detected by radioactivity counting in the Top-Count instrument.

Results: data were analysed and expressed as % inhibition referred to total activity of enzyme (=100%).

All compounds showing inhibition ≧50% were further analysed in order to study and define the kinetic-profile of inhibitor through Ki calculation.

The protocol used was the same described above, except for ATP and substrate concentrations. Either the concentration of ATP and histone Hi substrate were varied: 4, 8, 12, 24, 48 μM for ATP (containing proportionally diluted $P^{33}$g-ATP) and 0.4, 0.8, 1.2, 2.4, 4.8 μM for histone were used in absence and presence of two different, properly chosen inhibitor concentrations.

Experimental data were analysed by the computer program SigmaPlot for Ki determination, using a random bireactant system equation:

$$v = \frac{V\max \frac{(A)(B)}{aK_A K_B}}{1 + \frac{(A)}{K_A} + \frac{(B)}{K_B} + \frac{(A)(B)}{aK_A K_B}}$$

where A=ATP and B=histone H1.

The compounds of formula (I) of the present invention, suitable for administration to a mammal, e.g. to humans, can be administered by the usual routes and the dosage level depends upon the age, weight, conditions of the patient and the administration route.

For example, a suitable dosage adopted for oral administration of a compound of formula (I) may range from about 10 to about 500 mg pro dose, from 1 to 5 times daily. The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

In addition, the compounds of the invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, the compounds of the invention can be administered in combination with one or more chemotherapeutic agents such as, for instance, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, Sugen SU-5416, Sugen SU-6668, Herceptin, and the like, optionally within liposomal formulations thereof.

If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The present invention also includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic , magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. a starch, alginic alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty ester surfactant or lecithin.

The following examples illustrate but do not limit the present invention.

EXAMPLE 1

Preparation of N-[3-carbamoyl-4,5,6,7-tetrahydrobenzo[b]thien-2-yl]phenylacetamide (Compound 1)

A mixture of commercially available 2-amino-3-carbamoyl-4,5,6,7-tetrahydrobenzo[b]thiophene (5 mg, 0.026 mmol), phenylacetic acid (7 mg, 0.05 mmol), N-hydroxybenzotriazole (8.5 mg, 0.065 mmol), and N-cyclohexylcarbodiimide-N'-methylpolystyrene (loading about 1.5 mmol/g resin, 50 mg) in dichloromethane (2 ml)/dimethylformamide (0.5 ml) was agitated at 20° C. for 170 h. Afterward tris-(2-aminoethyl)-amine polystyrene (loading about 4 mmol/g resin 40 mg) was added for scavenging the hydroxybenzotriazole and the excess of acid, and the agitation was maintained for additional 24 h.

The resins were filtered, washed with dichloromethane, and the resulting solution was evapored to give 15 mg of crude material. The reaction mixture was purified by preparative high-pressure liquid chromatography using the following conditions:

| Eluent A: | aqueous solution of trifluoroacetic acid (0.01% v/v) | | |
|---|---|---|---|
| Eluent B: | acetonitril | | |
| Gradient: | Time (m) | % A | % B |
| | 0 (injection) | 90 | 10 |
| | 8 | 10 | 90 |
| | 10 (end) | 10 | 90 |
| Flow: | 20 ml/m | | |
| Column: | Waters Symmetry ™ C18 19 × 50 mm | | |
| Detector: | mass spectrometer, electrospray ionisation, positive mode. | | |

A liquid handler triggered by the mass spectrometer automatically collected the fractions containing the title compound. After evaporation of the solvent 3.4 mg of N-[3-carbamoyl-4,5,6,7-tetrahydrobenzo[b]thien-2-yl] phenylacetamide (colorless solid, $[M+H]^+=315$) were obtained.

By analogously reacting the 3-amino-thiophene derivative of formula (II), as reported in table I, each of which easily obtainable from the commercially available carboxylic ester, with the commercially available carboxylic acids of formula (III), reported in table 2, a library of N-[3-carbamoyl-4,5-substituted-thien-2-yl] amides of formula (I) was thus prepared.

Representative compounds of the library are reported in table 3.

TABLE 3 representative library compounds:

| n° | Compound | [M + H]⁺ |
|---|---|---|
| 2 | N-[3-carbamoyl-4,5,6,7-tetrahydrobenzo[b]thien-2-yl]acetamide; | 239 |
| 3 | N-[3-carbamoyl-4,5,6,7-tetrahydrobenzo[b]thien-2-yl]propionamide; | 253 |
| 4 | N-[3-carbamoyl-4,5,6,7-tetrahydrobenzo[b]thien-2-yl]2-butynoic amide; | 263 |
| 5 | N-[3-carbamoyl-4,5,6,7-tetrahydrobenzo[b]thien-2-yl]cyanoacetamide; | 267 |
| 6 | N-[3-carbamoyl-4,5,6,7-tetrahydrobenzo[b]thien-2-yl]cyclopropanecarboxamide; | 265 |
| 7 | N-[3-carbamoyl-4,5,6,7-tetrahydrobenzo[b]thien-2-yl]isobutyramide; | 267 |
| 8 | N-[3-carbamoyl-4,5,6,7-tetrahydrobenzo[b]thien-2-yl]3,3-dimethylacrylic amide; | 279 |
| 9 | N-[3-carbamoyl-4,5,6,7-tetrahydrobenzo[b]thien-2-yl]2-ketobutyramide; | 281 |
| 10 | N-[3-carbamoyl-4,5,6,7-tetrahydrobenzo[b]thien-2-yl]N,N-dimethylglycinamide; | 282 |
| 11 | N-[3-carbamoyl-4,5,6,7-tetrahydrobenzo[b]thien-2-yl]3-chloropropionamide; | 287 |
| 12 | N-[3-carbamoyl-4,5,6,7-tetrahydrobenzo[b]thien-2-yl]imidazol-4-carboxamide; | 291 |
| 13 | N-[3-carbamoyl-4,5,6,7-tetrahydrobenzo[b]thien-2-yl]pyrrole-2-carboxamide; | 290 |
| 14 | N-[3-carbamoyl-4,5,6,7-tetrahydrobenzo[b]thien-2-yl]cyclopentanecarboxamide; | 293 |
| 15 | N-[3-carbamoyl-4,5,6,7-tetrahydrobenzo[b]thien-2-yl]1-cyanocyclopropanecarboxamide; | 290 |
| 16 | N-[3-carbamoyl-4,5,6,7-tetrahydrobenzo[b]thien-2-yl]N-acetylglycinamide; | 296 |
| 17 | N-[3-carbamoyl-4,5,6,7-tetrahydrobenzo[b]thien-2-yl]pyrrole-3-carboxamide; | 290 |
| 18 | N-[3-carbamoyl-4,5,6,7-tetrahydrobenzo[b]thien-2-yl]benzamide; | 301 |
| 19 | N-[3-carbamoyl-4,5,6,7-tetrahydrobenzo[b]thien-2-yl]4-pyrazolecarboxamide; | 291 |
| 20 | N-[3-carbamoyl-4,5,6,7-tetrahydrobenzo[b]thien-2-yl]picolinic amide; | 302 |
| 21 | N-[3-carbamoyl-4,5,6,7-tetrahydrobenzo[b]thien-2-yl]nicotinic amide; | 302 |
| 22 | N-[3-carbamoyl-4,5,6,7-tetrahydrobenzo[b]thien-2-yl]isonicotinic amide; | 302 |
| 23 | N-[3-carbamoyl-4,5,6,7-tetrahydrobenzo[b]thien-2-yl]2-pyrazinecarboxamide; | 303 |
| 24 | N-[3-carbamoyl-4,5,6,7-tetrahydrobenzo[b]thien-2-yl]1-methylpyrrole-2-carboxamide; | 304 |
| 25 | N-[3-carbamoyl-4,5,6,7-tetrahydrobenzo[b]thien-2-yl]3-methyl-2-furoic amide; | 305 |
| 26 | N-[3-carbamoyl-4,5,6,7-tetrahydrobenzo[b]thien-2-yl]5-methylisoxazole-4-carboxamide; | 306 |
| 27 | N-[3-carbamoyl-4,5,6,7-tetrahydrobenzo[b]thien-2-yl]3-methylisoxazole-4-carboxamide; | 306 |
| 28 | N-[3-carbamoyl-4,5,6,7-tetrahydrobenzo[b]thien-2-yl]thiophene-2-carboxamide; | 307 |
| 29 | N-[3-carbamoyl-4,5,6,7-tetrahydrobenzo[b]thien-2-yl]thiophene-3-carboxamide; | 307 |
| 30 | N-[3-carbamoyl-4,5,6,7-tetrahydrobenzo[b]thien-2-yl]dl-pyroglutamic amide; | 308 |
| 31 | N-[3-carbamoyl-4,5,6,7-tetrahydrobenzo[b]thien-2-yl]1-(aminocarbonyl)-1-cyclopropanecarboxamide; | 308 |
| 32 | N-[3-carbamoyl-4,5,6,7-tetrahydrobenzo[b]thien-2-yl]o-toluic amide; | 315 |
| 33 | N-[3-carbamoyl-4,5,6,7-tetrahydrobenzo[b]thien-2-yl]5-methylisoxazole-3-carboxamide; | 306 |
| 34 | N-[3-carbamoyl-4,5,6,7-tetrahydrobenzo(b)thien-2-yl]m-toluic amide; | 315 |

TABLE 3-continued representative library compounds:

| n° | Compound | [M + H]⁺ |
|---|---|---|
| 35 | N-[3-carbamoyl-4,5,6,7-tetrahydrobenzo[b]thien-2-yl]3-aminopyrazole-4-carboxamide; | 306 |
| 36 | N-[3-carbamoyl-4,5,6,7-tetrahydrobenzo[b]thien-2-yl]p-toluic amide; | 315 |
| 37 | N-[3-carbamoyl-4,5,6,7-tetrahydrobenzo[b]thien-2-yl]salicylic amide; | 317 |
| 38 | N-[3-carbamoyl-4,5,6,7-tetrahydrobenzo[b]thien-2-yl]3-hydroxybenzamide; | 317 |
| 39 | N-[3-carbamoyl-5-isopropyl-thien-2-yl]cyclopentylacetamide; | 295 |
| 40 | N-[3-carbamoyl-5-isopropyl-thien-2-yl]4-hydroxybenzamide; | 305 |
| 41 | N-[3-carbamoyl-5-isopropyl-thien-2-yl]5-norbornene-2-carboxamide; | 305 |
| 42 | N-[3-carbamoyl-5-isopropyl-thien-2-yl]2-fluorobenzamide; | 307 |
| 43 | N-[3-carbamoyl-5-isopropyl-thien-2-yl]2-imidazolidone-4-carboxamide; | 297 |
| 44 | N-[3-carbamoyl-5-isopropyl-thien-2-yl]3-fluorobenzamide; | 307 |
| 45 | N-[3-carbamoyl-5-isopropyl-thien-2-yl]N'-acetyl-dl-alaninamide; | 298 |
| 46 | N-[3-carbamoyl-5-isopropyl-thien-2-yl]4-fluorobenzamide; | 307 |
| 47 | N-[3-carbamoyl-5-isopropyl-thien-2-yl]3-ureidopropionamide; | 299 |
| 48 | N-[3-carbamoyl-5-isopropyl-thien-2-yl]thiophene-2-acetamide; | 309 |
| 49 | N-[3-carbamoyl-5-isopropyl-thien-2-yl]thiophene-3-acetamide; | 309 |
| 50 | N-[3-carbamoyl-5-isopropyl-thien-2-yl]3-cyclopentylpropionamide; | 309 |
| 51 | N-[3-carbamoyl-5-isopropyl-thien-2-yl]cycloheptanecarboxamide; | 309 |
| 52 | N-[3-carbamoyl-5-isopropyl-thien-2-yl]2,2-dimethylhexanoic amide; | 311 |
| 53 | N-[3-carbamoyl-5-isopropyl-thien-2-yl]alpha-(isopropylideneaminooxy)propionamide; | 312 |
| 54 | N-[3-carbamoyl-5-isopropyl-thien-2-yl]N,N-dimethylsuccinamic amide; | 312 |
| 55 | N-[3-carbamoyl-5-isopropyl-thien-2-yl]urocanic amide; | 305 |
| 56 | N-[3-carbamoyl-5-isopropyl-thien-2-yl]phenylpropiolic amide; | 313 |
| 57 | N-[3-carbamoyl-5-isopropyl-thien-2-yl]2-methylpyrazine-5-carboxamide; | 305 |
| 58 | N-[3-carbamoyl-5-isopropyl-thien-2-yl]3-cyanobenzamide; | 314 |
| 59 | N-[3-carbamoyl-5-isopropyl-thien-2-yl]4-cyanobenzamide; | 314 |
| 60 | N-[3-carbamoyl-5-isopropyl-thien-2-yl]N-methyl-1-proline monohydrate; | 296 |
| 61 | N-[3-carbamoyl-5-isopropyl-thien-2-yl]cinnamic amide; | 315 |
| 62 | N-[3-carbamoyl-5-isopropyl-thien-2-yl]3-(3-pyridyl)acrylic amide; | 316 |
| 63 | N-[3-carbamoyl-5-isopropyl-thien-2-yl]3,5-dimethylisoxazole-4-carboxamide; | 308 |
| 64 | N-[3-carbamoyl-5-isopropyl-thien-2-yl]3-(4-pyridyl)-acrylic amide; | 316 |
| 65 | N-[3-carbamoyl-5-isopropyl-thien-2-yl]2,3-dimethylbenzamide; | 317 |
| 66 | N-[3-carbamoyl-5-isopropyl-thien-2-yl]2,4-dimethylbenzamide; | 317 |
| 67 | N-[3-carbamoyl-5-isopropyl-thien-2-yl]2,5-dimethylbenzamide; | 317 |
| 68 | N-[3-carbamoyl-5-isopropyl-thien-2-yl]2,6-dimethylbenzamide; | 317 |
| 69 | N-[3-carbamoyl-5-isopropyl-thien-2-yl]3,4-dimethylbenzamide; | 317 |
| 70 | N-[3-carbamoyl-5-isopropyl-thien-2-yl]3,5-dimethylbenzamide; | 317 |
| 71 | N-[3-carbamoyl-5-isopropyl-thien-2-yl]2-phenylpropionamide; | 317 |
| 72 | N-[3-carbamoyl-5-isopropyl-thien-2-yl]3- | 317 |

TABLE 3-continued representative library compounds:

| n° | Compound | [M + H]+ |
|---|---|---|
|  | phenylpropionamide; |  |
| 73 | N-[3-carbamoyl-5-isopropyl-thien-2-yl]N-carbamyl-dl-alpha-amino-n-butyramide; | 313 |
| 74 | N-[3-carbamoyl-5-isopropyl-thien-2-yl]o-tolylacetamide; | 317 |
| 75 | N-[3-carbamoyl-5-isopropyl-thien-2-yl]m-tolylacetamide; | 317 |
| 76 | N-[3-carbamoyl-5-isopropyl-thien-2-yl]p-tolylacetamide; | 317 |
| 77 | N-[3-carbamoyl-5-isopropyl-thien-2-yl]3-pyridinepropionamide; | 318 |
| 78 | N-[3-carbamoyl-5-phenyl-thien-2-yl]o-anisic amide; | 353 |
| 79 | N-[3-carbamoyl-5-phenyl-thien-2-yl]3-methylsalicylic amide; | 353 |
| 80 | N-[3-carbamoyl-5-phenyl-thien-2-yl]4-methylsalicylic amide; | 353 |
| 81 | N-[3-carbamoyl-5-phenyl-thien-2-yl]5-methylsalicylic amide; | 353 |
| 82 | N-[3-carbamoyl-5-phenyl-thien-2-yl]3-methoxybenzamide; | 353 |
| 83 | N-[3-carbamoyl-5-phenyl-thien-2-yl]3-hydroxy-4-methylbenzamide; | 353 |
| 84 | N-[3-carbamoyl-5-phenyl-thien-2-yl]p-anisic amide; | 353 |
| 85 | N-[3-carbamoyl-5-phenyl-thien-2-yl]phenoxy-acetamide; | 353 |
| 86 | N-[3-carbamoyl-5-phenyl-thien-2-yl]2-hydroxyphenylacetamide; | 353 |
| 87 | N-[3-carbamoyl-5-phenyl-thien-2-yl]3-hydroxyphenylacetamide; | 353 |
| 88 | N-[3-carbamoyl-5-phenyl-thien-2-yl]4-hydroxyphenylacetamide; | 353 |
| 89 | N-[3-carbamoyl-5-phenyl-thien-2-yl]dl-mandelic amide; | 353 |
| 90 | N-[3-carbamoyl-5-phenyl-thien-2-yl]3-hydroxy-o-toluic amide; | 353 |
| 91 | N-[3-carbamoyl-5-phenyl-thien-2-yl]alpha-fluorophenylacetamide; | 355 |
| 92 | N-[3-carbamoyl-5-phenyl-thien-2-yl]2-fluorophenylacetamide; | 355 |
| 93 | N-[3-carbamoyl-5-phenyl-thien-2-yl]3-fluorophenylacetamide; | 355 |
| 94 | N-[3-carbamoyl-5-phenyl-thien-2-yl]4-fluorophenylacetamide; | 355 |
| 95 | N-[3-carbamoyl-5-phenyl-thien-2-yl]3-(2-thienyl)acrylic amide; | 355 |
| 96 | N-[3-carbamoyl-5-phenyl-thien-2-yl]3-(3-thienyl)-acrylic amide; | 355 |
| 97 | N-[3-carbamoyl-5-phenyl-thien-2-yl]3-(2-thienyl)propanoic amide; | 357 |
| 98 | N-[3-carbamoyl-5-phenyl-thien-2-yl]2-chlorobenzamide; | 357 |
| 99 | N-[3-carbamoyl-5-phenyl-thien-2-yl]3-chlorobenzamide; | 357 |
| 100 | N-[3-carbamoyl-5-phenyl-thien-2-yl]4-chlorobenzamide; | 357 |
| 101 | N-[3-carbamoyl-5-phenyl-thien-2-yl]N-propylmaleamic amide; | 358 |
| 102 | N-[3-carbamoyl-5-phenyl-thien-2-yl]N'-acetyl-dl-allylglycinamide; | 358 |
| 103 | N-[3-carbamoyl-5-phenyl-thien-2-yl]N'-acetyl-dl-prolinamide; | 358 |
| 104 | N-[3-carbamoyl-5-phenyl-thien-2-yl]3-(1-piperidine)propionamide; | 358 |
| 105 | N-[3-carbamoyl-5-phenyl-thien-2-yl]2-chloronicotinic amide; | 358 |
| 106 | N-[3-carbamoyl-5-phenyl-thien-2-yl]6-chloronicotinic amide; | 358 |
| 107 | N-[3-carbamoyl-5-phenyl-thien-2-yl]N-(acetoacetyl)glycinamide; | 360 |
| 108 | N-[3-carbamoyl-5-phenyl-thien-2-yl]N'-acetyl-dl-valinamide; | 360 |
| 109 | N-[3-carbamoyl-5-phenyl-thien-2-yl]dl-alanyl-dl-alanine; | 361 |
| 110 | N-[3-carbamoyl-5-phenyl-thien-2-yl]indole-6-carboxamide; | 362 |
| 111 | N-[3-carbamoyl-5-phenyl-thien-2-yl]benzofuran-2-carboxamide; | 363 |
| 112 | N-[3-carbamoyl-5-phenyl-thien-2-yl]1-phenyl-1-cyclopropanecarboxamide; | 363 |
| 113 | N-[3-carbamoyl-5-phenyl-thien-2-yl]cycloheptylacetamide; | 357 |
| 114 | N-[3-carbamoyl-5-phenyl-thien-2-yl]alpha-methylcinnamic amide; | 363 |
| 115 | N-[3-carbamoyl-5-phenyl-thien-2-yl]2-acetylbenzamide; | 365 |
| 116 | N-[3-carbamoyl-5-benzyl-thien-2-yl]4-acetylbenzamide; | 379 |
| 117 | N-[3-carbamoyl-5-benzyl-thien-2-yl]o-coumaric amide; | 379 |
| 118 | N-[3-carbamoyl-5-benzyl-thien-2-yl]3-hydroxycinnamic amide; | 379 |
| 119 | N-[3-carbamoyl-5-benzyl-thien-2-yl]4-hydroxycinnamic amide; | 379 |
| 120 | N-[3-carbamoyl-5-benzyl-thien-2-yl]p-coumaric amide; | 379 |
| 121 | N-[3-carbamoyl-5-benzyl-thien-2-yl]4-isopropylbenzamide; | 379 |
| 122 | N-[3-carbamoyl-5-benzyl-thien-2-yl]2-(3,5-xylyl)acetamide; | 379 |
| 123 | N-[3-carbamoyl-5-benzyl-thien-2-yl]phthalamic amide; | 380 |
| 124 | N-[3-carbamoyl-5-benzyl-thien-2-yl]N-carbamoylmaleamic amide; | 373 |
| 125 | N-[3-carbamoyl-5-benzyl-thien-2-yl]3-dimethylaminobenzamide; | 380 |
| 126 | N-[3-carbamoyl-5-benzyl-thien-2-yl]4-dimethylaminobenzamide; | 380 |
| 127 | N-[3-carbamoyl-5-benzyl-thien-2-yl]2-dimethylaminobenzamide; | 380 |
| 128 | N-[3-carbamoyl-5-benzyl-thien-2-yl]N'-carbamyl-dl-norvalinamide; | 375 |
| 129 | N-[3-carbamoyl-5-benzyl-thien-2-yl]piperonylic amide; | 381 |
| 130 | N-[3-carbamoyl-5-benzyl-thien-2-yl]N-carbamyl-dl-valine; | 375 |
| 131 | N-[3-carbamoyl-5-benzyl-thien-2-yl]alpha-fluorocinnamic amide; | 381 |
| 132 | N-[3-carbamoyl-5-benzyl-thien-2-yl]3-methoxy-4-methylbenzamide; | 381 |
| 133 | N-[3-carbamoyl-5-benzyl-thien-2-yl]indole-2-carboxamide; | 376 |
| 134 | N-[3-carbamoyl-5-benzyl-thien-2-yl]4-hydroxy-3,5-dimethylbenzamide; | 381 |
| 135 | N-[3-carbamoyl-5-benzyl-thien-2-yl]indole-3-carboxamide; | 376 |
| 136 | N-[3-carbamoyl-5-benzyl-thien-2-yl]benzyloxyacetamide; | 381 |
| 137 | N-[3-carbamoyl-5-benzyl-thien-2-yl]indole-5-carboxamide; | 376 |
| 138 | N-[3-carbamoyl-5-benzyl-thien-2-yl]4-dimethylaminobutyramide; | 346 |
| 139 | N-[3-carbamoyl-5-benzyl-thien-2-yl]indole-4-carboxamide; | 376 |
| 140 | N-[3-carbamoyl-5-benzyl-thien-2-yl]3-methoxysalicylic amide; | 383 |
| 141 | N-[3-carbamoyl-5-benzyl-thien-2-yl]4-methoxysalicylic amide; | 383 |
| 142 | N-[3-carbamoyl-5-benzyl-thien-2-yl]5-methoxysalicylic amide; | 383 |
| 143 | N-[3-carbamoyl-5-benzyl-thien-2-yl]5-benzimidazolecarboxamide; | 377 |
| 144 | N-[3-carbamoyl-5-benzyl-thien-2-yl]3-hydroxy-4-methoxybenzamide; | 383 |
| 145 | N-[3-carbamoyl-5-benzyl-thien-2-yl]indazole-3-carboxamide; | 377 |
| 146 | N-[3-carbamoyl-5-benzyl-thien-2-yl]vanillic amide; | 383 |
| 147 | N-[3-carbamoyl-5-benzyl-thien-2-yl]4-hydroxyphenoxyacetamide; | 385 |
| 148 | N-[3-carbamoyl-5-benzyl-thien-2-yl]6-methoxysalicylic amide; | 383 |
| 149 | N-[3-carbamoyl-5-benzyl-thien-2-yl]4- | 341 |

TABLE 3-continued representative library compounds:

| n° | Compound | [M + H]⁺ |
|---|---|---|
| | imidazoleacetamide; | |
| 150 | N-[3-carbamoyl-5-benzyl-thien-2-yl]N-(2-furoyl)glycinamide; | 384 |
| 151 | N-[3-carbamoyl-5-benzyl-thien-2-yl]6-carboxypurine; | 379 |
| 152 | N-[3-carbamoyl-5-benzyl-thien-2-yl]beta-maleimidopropionamide; | 384 |
| 153 | N-[3-carbamoyl-5-benzyl-thien-2-yl]3,4-dihydro-2,2-dimethyl-4-oxo-2h-pyran-6-carboxamide; | 385 |
| 154 | N-[3-carbamoyl-5-(1-phenylethyl)-thien-2-yl]1-acetylpiperidine-4-carboxamide; | 400 |
| 155 | N-[3-carbamoyl-5-(1-phenylethyl)-thien-2-yl]1-naphthoic amide; | 401 |
| 156 | N-[3-carbamoyl-5-(1-phenylethyl)-thien-2-yl]2-naphthoic amide; | 401 |
| 157 | N-[3-carbamoyl-5-(1-phenylethyl)-thien-2-yl]4-chlorosalicylic amide; | 401 |
| 158 | N-[3-carbamoyl-5-(1-phenylethyl)-thien-2-yl]5-chlorosalicylic amide; | 401 |
| 159 | N-[3-carbamoyl-5-(1-phenylethyl)-thien-2-yl]3-chloro-4-hydroxybenzamide; | 401 |
| 160 | N-[3-carbamoyl-5-(1-phenylethyl)-thien-2-yl]3-chlorosalicylic amide; | 401 |
| 161 | N-[3-carbamoyl-5-(1-phenylethyl)-thien-2-yl]N'-acetyl-hydroxyproline; | 402 |
| 162 | N-[3-carbamoyl-5-(1-phenylethyl)-thien-2-yl]quinaldic amide; | 402 |
| 163 | N-[3-carbamoyl-5-(1-phenylethyl)-thien-2-yl]quinoline-3-carboxamide; | 402 |
| 164 | N-[3-carbamoyl-5-(1-phenylethyl)-thien-2-yl]quinoline-4-carboxamide; | 402 |
| 165 | N-[3-carbamoyl-5-(1-phenylethyl)-thien-2-yl]1-isoquinolinecarboxamide; | 402 |
| 166 | N-[3-carbamoyl-5-(1-phenylethyl)-thien-2-yl]quinoline-6-carboxamide; | 402 |
| 167 | N-[3-carbamoyl-5-(1-phenylethyl)-thien-2-yl]quinoline-8-carboxamide; | 402 |
| 168 | N-[3-carbamoyl-5-(1-phenylethyl)-thien-2-yl]6-acetamidohexanoic amide; | 402 |
| 169 | N-[3-carbamoyl-5-(1-phenylethyl)-thien-2-yl]N'-acetyl-dl-leucinamide; | 402 |
| 170 | N-[3-carbamoyl-5-(1-phenylethyl)-thien-2-yl]N',N'-di-n-propyl-l-alaninamide; | 402 |
| 171 | N-[3-carbamoyl-5-(1-phenylethyl)-thien-2-yl]N'-alpha-acetyl-l-asparaginamide; | 403 |
| 172 | N-[3-carbamoyl-5-(1-phenylethyl)-thien-2-yl]cinnoline-4-carboxamide; | 403 |
| 173 | N-[3-carbamoyl-5-(1-phenylethyl)-thien-2-yl]2-quinoxalinecarboxamide; | 403 |
| 174 | N-[3-carbamoyl-5-(1-phenylethyl)-thien-2-yl]3-methylindene-2-carboxamide; | 403 |
| 175 | N-[3-carbamoyl-5-(1-phenylethyl)-thien-2-yl]1-methylindole-2-carboxamide; | 404 |
| 176 | N-[3-carbamoyl-5-(1-phenylethyl)-thien-2-yl]1-methylindole-3-carboxamide; | 404 |
| 177 | N-[3-carbamoyl-5-(1-phenylethyl)-thien-2-yl]indazolone-4-carboxamide; | 405 |
| 178 | N-[3-carbamoyl-5-(1-phenylethyl)-thien-2-yl]3-oxo-1-indancarboxamide; | 405 |
| 179 | N-[3-carbamoyl-5-(1-phenylethyl)-thien-2-yl]1,2,3,4-tetrahydro-2-naphthoic amide; | 405 |
| 180 | N-[3-carbamoyl-5-(1-phenylethyl)-thien-2-yl]2-indanylacetamide; | 405 |
| 181 | N-[3-carbamoyl-5-(1-phenylethyl)-thien-2-yl]1-methyl-4-imidazole-acetamide; | 369 |
| 182 | N-[3-carbamoyl-5-(1-phenylethyl)-thien-2-yl]arecaidinamide; | 370 |
| 183 | N-[3-carbamoyl-5-(1-phenylethyl)-thien-2-yl]3-benzoylpropionamide; | 407 |
| 184 | N-[3-carbamoyl-5-(1-phenylethyl)-thien-2-yl]4-methoxycinnamic amide; | 407 |
| 185 | N-[3-carbamoyl-5-(1-phenylethyl)-thien-2-yl]2-methoxycinnamic amide; | 407 |
| 186 | N-[3-carbamoyl-5-(1-phenylethyl)-thien-2-yl]benzo[b]thiophene-2-carboxamide; | 407 |
| 187 | N-[3-carbamoyl-5-(1-phenylethyl)-thien-2-yl]2-isopropyl-2-phenylacetamide; | 407 |
| 188 | N-[3-carbamoyl-5-(1-phenylethyl)-thien-2-yl]N'-acetylanthranilic amide; | 408 |
| 189 | N-[3-carbamoyl-5-(1-phenylethyl)-thien-2-yl]4-acetamidobenzamide; | 408 |
| 190 | N-[3-carbamoyl-5-(1-phenylethyl)-thien-2-yl]hippuric amide; | 408 |
| 191 | N-[3-carbamoyl-5-(1-phenylethyl)-thien-2-yl]3-acetamidobenzamide; | 408 |
| 192 | N-[3-carbamoyl-4,5-dimethyl-thien-2-yl]3,4-methylenedioxyphenylacetamide; | 333 |
| 193 | N-[3-carbamoyl-4,5-dimethyl-thien-2-yl]nicotinuric amide; | 333 |
| 194 | N-[3-carbamoyl-4,5-dimethyl-thien-2-yl]4-isopropoxybenzamide; | 333 |
| 195 | N-[3-carbamoyl-4,5-dimethyl-thien-2-yl]3-(diethylamino)propionamide; | 298 |
| 196 | N-[3-carbamoyl-4,5-dimethyl-thien-2-yl]2,5-dimethoxybenzamide; | 335 |
| 197 | N-[3-carbamoyl-4,5-dimethyl-thien-2-yl]2,6-dimethoxybenzamide; | 335 |
| 198 | N-[3-carbamoyl-4,5-dimethyl-thien-2-yl]3,4-dimethoxybenzamide; | 335 |
| 199 | N-[3-carbamoyl-4,5-dimethyl-thien-2-yl]3,5-dimethoxybenzamide; | 335 |
| 200 | N-[3-carbamoyl-4,5-dimethyl-thien-2-yl]2-methoxyphenoxyacetamide; | 335 |
| 201 | N-[3-carbamoyl-4,5-dimethyl-thien-2-yl]1-thymineacetamide; | 337 |
| 202 | N-[3-carbamoyl-4,5-dimethyl-thien-2-yl]indole-3-acetamide; | 328 |
| 203 | N-[3-carbamoyl-4,5-dimethyl-thien-2-yl]3-(2-thenoyl)-propionamide; | 337 |
| 204 | N-[3-carbamoyl-4,5-dimethyl-thien-2-yl]3-chloro-4-methoxybenzamide; | 339 |
| 205 | N-[3-carbamoyl-4,5-dimethyl-thien-2-yl]5-methylindole-2-carboxamide; | 328 |
| 206 | N-[3-carbamoyl-4,5-dimethyl-thien-2-yl]5-chloro-2-methoxybenzamide; | 339 |
| 207 | N-[3-carbamoyl-4,5-dimethyl-thien-2-yl]1-(2-carboxyphenyl)pyrrole; | 340 |
| 208 | N-[3-carbamoyl-4,5-dimethyl-thien-2-yl]4-(1-H-pyrrol-1-yl)benzamide; | 340 |
| 209 | N-[3-carbamoyl-4,5-dimethyl-thien-2-yl]1-methyl-3-indoleacetamide; | 342 |
| 210 | N-[3-carbamoyl-4,5-dimethyl-thien-2-yl]2-methyl-1h-benzimidazole-5-carboxamide; | 329 |
| 211 | N-[3-carbamoyl-4,5-dimethyl-thien-2-yl]2-(trifluoromethyl)benzamide; | 343 |
| 212 | N-[3-carbamoyl-4,5-dimethyl-thien-2-yl]3-(trifluoromethyl)benzamide; | 343 |
| 213 | N-[3-carbamoyl-4,5-dimethyl-thien-2-yl]4-(trifluoromethyl)benzamide; | 343 |
| 214 | N-[3-carbamoyl-4,5-dimethyl-thien-2-yl]chromone-2-carboxamide; | 343 |
| 215 | N-[3-carbamoyl-4,5-dimethyl-thien-2-yl]5-hydroxyindole-2-carboxamide; | 330 |
| 216 | N-[3-carbamoyl-4,5-dimethyl-thien-2-yl]chromone-3-carboxamide; | 343 |
| 217 | N-[3-carbamoyl-4,5-dimethyl-thien-2-yl]3-hydroxy-2-quinoxalinecarboxamide; | 343 |
| 218 | N-[3-carbamoyl-4,5-dimethyl-thien-2-yl]1-phenyl-1-cyclopentanecarboxamide; | 343 |
| 219 | N-[3-carbamoyl-4,5-dimethyl-thien-2-yl]2,3-dichlorobenzamide; | 344 |
| 220 | N-[3-carbamoyl-4,5-dimethyl-thien-2-yl]2,4-dichlorobenzamide; | 344 |
| 221 | N-[3-carbamoyl-4,5-dimethyl-thien-2-yl]2,5-dichlorobenzamide; | 344 |
| 222 | N-[3-carbamoyl-4,5-dimethyl-thien-2-yl]2,6-dichlorobenzamide; | 344 |
| 223 | N-[3-carbamoyl-4,5-dimethyl-thien-2-yl]3,4-dichlorobenzamide; | 344 |
| 224 | N-[3-carbamoyl-4,5-dimethyl-thien-2-yl]3,5-dichlorobenzamide; | 344 |

TABLE 3-continued representative library compounds:

| n° | Compound | [M + H]+ |
|---|---|---|
| 225 | N-[3-carbamoyl-4,5-dimethyl-thien-2-yl]4-oxophenylamino-2-butenoic amide; | 344 |
| 226 | N-[3-carbamoyl-4,5-dimethyl-thien-2-yl]4-(dimethylamino)cinnamic amide; | 344 |
| 227 | N-[3-carbamoyl-4,5-dimethyl-thien-2-yl]N'-chloroacetyl-dl-2-amino-n-butyramide; | 332 |
| 228 | N-[3-carbamoyl-4,5-dimethyl-thien-2-yl]3,4-methylenedioxycinnamic amide; | 345 |
| 229 | N-[3-carbamoyl-4,5-dimethyl-thien-2-yl]7-methoxybenzofuran-2-carboxamide; | 345 |
| 230 | N-[3-carbamoyl-4,5-dimethyl-thien-2-yl]4-benzoylbutyramide; | 345 |
| 231 | N-[3-carbamoyl-4-methyl-thien-2-yl]benzo[b]thiophene-3-acetamide; | 331 |
| 232 | N-[3-carbamoyl-4-methyl-thien-2-yl]N'-benzoyl-beta-alaninamide; | 332 |
| 233 | N-[3-carbamoyl-4-methyl-thien-2-yl]N'-acetyl-dl-phenylglycinamide; | 332 |
| 234 | N-[3-carbamoyl-4-methyl-thien-2-yl]N'-benzoyl-dl-alaninamide; | 332 |
| 235 | N-[3-carbamoyl-4-methyl-thien-2-yl]N'-methylhippuric amide; | 332 |
| 236 | N-[3-carbamoyl-4-methyl-thien-2-yl]o-hydroxy-hippuric amide; | 334 |
| 237 | N-[3-carbamoyl-4-methyl-thien-2-yl]N'-(furan-2-yl-acryl)-glycinamide; | 334 |
| 238 | N-[3-carbamoyl-4-methyl-thien-2-yl](3,5-dimethoxyphenyl)acetamide; | 335 |
| 239 | N-[3-carbamoyl-4-methyl-thien-2-yl]3,5-dimethoxy-4-methylbenzamide; | 335 |
| 240 | N-[3-carbamoyl-4-methyl-thien-2-yl](2,4-dimethoxy-phenyl)-acetamide; | 335 |
| 241 | N-[3-carbamoyl-4-methyl-thien-2-yl]5-(2-thienoyl)butyramide; | 337 |
| 242 | N-[3-carbamoyl-4-methyl-thien-2-yl]4-(methylsulfonyl)benzamide; | 339 |
| 243 | N-[3-carbamoyl-4-methyl-thien-2-yl]phenylsulphonylacetamide; | 339 |
| 244 | N-[3-carbamoyl-4-methyl-thien-2-yl]3-indolepropionamide; | 328 |
| 245 | N-[3-carbamoyl-4-methyl-thien-2-yl]3-(methylsulfonyl)benzamide; | 339 |
| 246 | N-[3-carbamoyl-4-methyl-thien-2-yl]2-methyl-3-indoleacetamide; | 328 |
| 247 | N-[3-carbamoyl-4-methyl-thien-2-yl]2-(methylsulfonyl)benzamide; | 339 |
| 248 | N-[3-carbamoyl-4-methyl-thien-2-yl]4-sulfonamidobenzamide; | 340 |
| 249 | N-[3-carbamoyl-4-methyl-thien-2-yl]5-methyl-1-phenylpyrazole-4-carboxamide; | 341 |
| 250 | N-[3-carbamoyl-4-methyl-thien-2-yl]5-methyl-3-phenylisoxazole-4-carboxamide; | 342 |
| 251 | N-[3-carbamoyl-4-methyl-thien-2-yl]2-hydroxy-5-(1 h-pyrrol-1-yl)benzamide; | 342 |
| 252 | N-[3-carbamoyl-4-methyl-thien-2-yl]4-methyl-2-phenyl-1,2,3-triazole-5-carboxamide; | 342 |
| 253 | N-[3-carbamoyl-4-methyl-thien-2-yl]N'-acetyl-dl-phenylglycinamide; | 346 |
| 254 | N-[3-carbamoyl-4-methyl-thien-2-yl]2,3-dimethoxycinnamic amide; | 347 |
| 255 | N-[3-carbamoyl-4-methyl-thien-2-yl]2-benzimidazolepropionamide; | 329 |
| 256 | N-[3-carbamoyl-4-methyl-thien-2-yl]2,5-dimethoxycinnamic amide; | 347 |
| 257 | N-[3-carbamoyl-4-methyl-thien-2-yl]3,4-dimethoxycinnamic amide; | 347 |
| 258 | N-[3-carbamoyl-4-methyl-thien-2-yl]3,5-dimethoxycinnamic amide; | 347 |
| 259 | N-[3-carbamoyl-4-methyl-thien-2-yl]2,4-dimethoxycinnamic amide; | 347 |
| 260 | N-[3-carbamoyl-4-methyl-thien-2-yl]3-(3,4-dimethoxyphenyl)propionamide; | 349 |
| 261 | N-[3-carbamoyl-4-methyl-thien-2-yl]9-fluorenecarboxamide; | 349 |
| 262 | N-[3-carbamoyl-4-methyl-thien-2-yl]6-chloro(2H)-1-benzopyran-3-carboxamide; | 349 |
| 263 | N-[3-carbamoyl-4-methyl-thien-2-yl]epsilon-maleimidocaproic amide; | 350 |
| 264 | N-[3-carbamoyl-4-methyl-thien-2-yl]5-methoxyindole-2-carboxamide; | 330 |
| 265 | N-[3-carbamoyl-4-methyl-thien-2-yl]2,3,4-trimethoxybenzamide; | 351 |
| 266 | N-[3-carbamoyl-4-methyl-thien-2-yl]5-hydroxyindole-3-acetamide; | 330 |
| 267 | N-[3-carbamoyl-4-methyl-thien-2-yl]2,4,5-trimethoxybenzamide; | 351 |
| 268 | N-[3-carbamoyl-6-methyl-4,5,6,7-tetrahydrothieno[2,3-c]pyridin-2-yl]3,4,5-trimethoxybenzamide; | 406 |
| 269 | N-[3-carbamoyl-6-methyl-4,5,6,7-tetrahydrothieno[2,3-c]pyridin-2-yl]2,4,6-trimethoxybenzamide; | 406 |
| 270 | N-[3-carbamoyl-6-methyl-4,5,6,7-tetrahydrothieno[2,3-c]pyridin-2-yl]3-chlorobenzo[b]thiophene-2-carboxamide; | 406 |
| 271 | N-[3-carbamoyl-6-methyl-4,5,6,7-tetrahydrothieno[2,3-c]pyridin-2-yl]3-(phenylsulfonyl)propionamide; | 408 |
| 272 | N-[3-carbamoyl-6-methyl-4,5,6,7-tetrahydrothieno[2,3-c]pyridin-2-yl]4-toluenesulfonylacetamide; | 408 |
| 273 | N-[3-carbamoyl-6-methyl-4,5,6,7-tetrahydrothieno[2,3-c]pyridin-2-yl]4-methylsulfonylphenylacetamide; | 408 |
| 274 | N-[3-carbamoyl-6-methyl-4,5,6,7-tetrahydrothieno[2,3-c]pyridin-2-yl]5-fluoroindole-3-acetamide; | 387 |
| 275 | N-[3-carbamoyl-6-methyl-4,5,6,7-tetrahydrothieno[2,3-c]pyridin-2-yl]3-phthalimido-propionamide; | 413 |
| 276 | N-[3-carbamoyl-6-methyl-4,5,6,7-tetrahydrothieno[2,3-c]pyridin-2-yl]5-methoxy-2-methyl-3-indoleacetamide; | 417 |
| 277 | N-[3-carbamoyl-6-methyl-4,5,6,7-tetrahydrothieno[2,3-c]pyridin-2-yl]5-methoxy-1-indanone-3-acetamide; | 414 |
| 278 | N-[3-carbamoyl-6-methyl-4,5,6,7-tetrahydrothieno[2,3-c]pyridin-2-yl]5-(4-chlorophenyl)-2-furoic amide; | 416 |
| 279 | N-[3-carbamoyl-6-methyl-4,5,6,7-tetrahydrothieno[2,3-c]pyridin-2-yl]6-chlorokynurenic amide; | 417 |
| 280 | N-[3-carbamoyl-6-methyl-4,5,6,7-tetrahydrothieno[2,3-c]pyridin-2-yl]N'-(4-chlorophenyl)maleamic amide; | 419 |
| 281 | N-[3-carbamoyl-6-methyl-4,5,6,7-tetrahydrothieno[2,3-c]pyridin-2-yl]N'-p-tosylglycinamide; | 423 |
| 282 | N-[3-carbamoyl-6-methyl-4,5,6,7-tetrahydrothieno[2,3-c]pyridin-2-yl]5-chloroindole-2-carboxamide; | 389 |
| 283 | N-[3-carbamoyl-6-methyl-4,5,6,7-tetrahydrothieno[2,3-c]pyridin-2-yl]N'-(1-naphthyl)maleamic amide; | 435 |
| 284 | N-[3-carbamoyl-6-methyl-4,5,6,7-tetrahydrothieno[2,3-c]pyridin-2-yl]3-iodobenzamide; | 442 |
| 285 | N-[3-carbamoyl-6-methyl-4,5,6,7-tetrahydrothieno[2,3-c]pyridin-2-yl]4-iodobenzamide; | 442 |
| 286 | N-[3-carbamoyl-6-methyl-4,5,6,7-tetrahydrothieno[2,3-c]pyridin-2-yl]N-m-tolylphthalamic amide; | 449 |
| 287 | N-[3-carbamoyl-6-methyl-4,5,6,7-tetrahydrothieno[2,3-c]pyridin-2-yl]N'-acetyl-dl-histidine; | 391 |
| 288 | N-[3-carbamoyl-6-methyl-4,5,6,7-tetrahydrothieno[2,3-c]pyridin-2-yl]3-acetamino-6-bromobenzamide; | 452 |
| 289 | N-[3-carbamoyl-6-methyl-4,5,6,7-tetrahydrothieno[2,3-c]pyridin-2-yl]2-acetamido-5-bromobenzamide; | 452 |

TABLE 3-continued representative library compounds:

| n° | Compound | [M + H]+ |
|---|---|---|
| 290 | N-[3-carbamoyl-6-methyl-4,5,6,7-tetrahydrothieno[2,3-c]pyridin-2-yl]2-iodophenylacetamide; | 456 |
| 291 | N-[3-carbamoyl-6-methyl-4,5,6,7-tetrahydrothieno[2,3-c]pyridin-2-yl]4-iodophenylacetamide; | 456 |
| 292 | N-[3-carbamoyl-6-methyl-4,5,6,7-tetrahydrothieno[2,3-c]pyridin-2-yl]8-(3-carboxamidopropyl)-1,3-dimethylxanthine; | 460 |
| 293 | N-[3-carbamoyl-6-methyl-4,5,6,7-tetrahydrothieno[2,3-c]pyridin-2-yl]7-bromokynurenic amide; | 462 |
| 294 | N-[3-carbamoyl-6-methyl-4,5,6,7-tetrahydrothieno[2,3-c]pyridin-2-yl]N'-benzoyl-dl-phenylalaninamide. | 463 |
| 295 | N-[3-carbamoyl-6-methyl-4,5,6,7-tetrahydrothieno[2,3-c]pyridin-2-yl]indole-3-butyramide; | 397 |
| 296 | N-[3-carbamoyl-6-methyl-4,5,6,7-tetrahydrothieno[2,3-c]pyridin-2-yl]4-chloroindole-3-acetamide; | 403 |
| 297 | N-[3-carbamoyl-6-methyl-4,5,6,7-tetrahydrothieno[2,3-c]pyridin-2-yl]dl-desthiobiotin; | 408 |
| 298 | N-[3-carbamoyl-6-methyl-4,5,6,7-tetrahydrothieno[2,3-c]pyridin-2-yl]4,6-dichloroindole-2-carboxamide; | 424 |
| 299 | N-[3-carbamoyl-6-methyl-4,5,6,7-tetrahydrothieno[2,3-c]pyridin-2-yl]N'-benzoyl-histidinamide | 453 |

What is claimed is:

1. A 3-aminocarbonyl-2-carboxamido-thiophene compound having the formula (I):

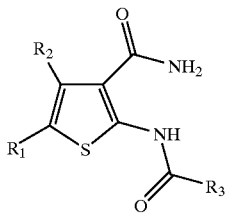

(I)

wherein:
   $R_1$ and $R_2$ are, independently from each other, hydrogen, halogen or an optionally substituted group comprising aryl, straight or branched $C_1$–$C_6$ alkyl or aryl $C_1$–$C_6$ alkyl;
   $R_3$ is an optionally substituted group comprising:
      i) straight or branched $C_1$–$C_8$ alkyl, $C_2$–$C_6$ alkenyl, $C_2$–$C_6$ alkynyl or $C_2$–$C_6$ alkylcarbonyl;
      ii) aryl;
      iii) 3 to 7 membered carbocycle; or
      iv) 5 to 7 membered heterocycle with from 1 to 3 heteroatoms of nitrogen, oxygen or sulfur;
or a pharmaceutically acceptable salt thereof, provided that:
   a) when $R_1$ is phenyl and $R_2$ is hydrogen, $R_3$ is other than phenyl or methyl;
   b) when $R_1$ and $R_2$ are both methyl, $R_3$ is other than p-methoxyphenyl;
   c') when $R_1$ is phenyl, $R_3$ is other than $C_1$–$C_6$ alkyl; and
   d') when $R_1$ is hydrogen and $R_2$ is methyl, $R_3$ is other than n-propyl or n-butyl.

2. The compound of claim 1, wherein $R_1$ and $R_2$ are, each independently, hydrogen, $C_1$–$C_4$ alkyl or optionally substituted aryl or aryl $C_1$–$C_4$ aryl.

3. The compound of claim 1, wherein $R_1$ is selected from the group consisting of isopropyl, phenyl, phenylmethyl and 1-phenylethyl; and $R_2$ is hydrogen.

4. The compound of claim 1, wherein $R_1$ is hydrogen; and $R_2$ is selected from the group consisting of methyl and 4-fluorophenyl.

5. A thiophene compound selected from the group consisting of:
   N-[3-carbamoyl-5-isopropyl-thien-2-yl]cyclopentylacetamide;
   N-[3-carbamoyl-5-isopropyl-thien-2-yl]4-hydroxybenzamide;
   N-[3-carbamoyl-5-isopropyl-thien-2-yl]5-norbornene-2-carboxamide;
   N-[3-carbamoyl-5-isopropyl-thien-2-yl]2-fluorobenzamide;
   N-[3-carbamoyl-5-isopropyl-thien-2-yl]2-imidazolidone-4-carboxamide;
   N-[3-carbamoyl-5-isopropyl-thien-2-yl]3-fluorobenzamide;
   N-[3-carbamoyl-5-isopropyl-thien-2-yl]N'-acetyl-dl-alaninamide;
   N-[3-carbamoyl-5-isopropyl-thien-2-yl]4-fluorobenzamide;
   N-[3-carbamoyl-5-isopropyl-thien-2-yl]3-ureidopropionamide;
   N-[3-carbamoyl-5-isopropyl-thien-2-yl]thiophene-2-acetamide;
   N-[3-carbamoyl-5-isopropyl-thien-2-yl]thiophene-3-acetamide;
   N-[3-carbamoyl-5-isopropyl-thien-2-yl]3-cyclopentylpropionamide;
   N-[3-carbamoyl-5-isopropyl-thien-2-yl]cycloheptanecarboxamide;
   N-[3-carbamoyl-5-isopropyl-thien-2-yl]2,2-dimethylhexanoic amide;
   N-[3-carbamoyl-5-isopropyl-thien-2-yl]alpha-(isopropylideneaminooxy)propionamide;
   N-[3-carbamoyl-5-isopropyl-thien-2-yl]N,N-dimethylsuccinamic amide;
   N-[3-carbamoyl-5-isopropyl-thien-2-yl]urocanic amide;
   N-[3-carbamoyl-5-isopropyl-thien-2-yl]phenylpropiolic amide;
   N-[3-carbamoyl-5-isopropyl-thien-2-yl]2-methylpyrazine-5-carboxamide;
   N-[3-carbamoyl-5-isopropyl-thien-2-yl]3-cyanobenzamide;
   N-[3-carbamoyl-5-isopropyl-thien-2-yl]4-cyanobenzamide;
   N-[3-carbamoyl-5-isopropyl-thien-2-yl]N-methyl-1-proline monohydrate;
   N-[3-carbamoyl-5-isopropyl-thien-2-yl]cinnamic amide;
   N-[3-carbamoyl-5-isopropyl-thien-2-yl]3-(3-pyridyl)acrylic amide;
   N-[3-carbamoyl-5-isopropyl-thien-2-yl]3,5-dimethylisoxazole-4-carboxamide;
   N-[3-carbamoyl-5-isopropyl-thien-2-yl]3-(4-pyridyl)-acrylic amide;
   N-[3-carbamoyl-5-isopropyl-thien-2-yl]2,3-dimethylbenzamide;
   N-[3-carbamoyl-5-isopropyl-thien-2-yl]2,4-dimethylbenzamide;
   N-[3-carbamoyl-5-isopropyl-thien-2-yl]2,5-dimethylbenzamide;
   N-[3-carbamoyl-5-isopropyl-thien-2-yl]2,6-dimethylbenzamide;
   N-[3-carbamoyl-5-isopropyl-thien-2-yl]3,4-dimethylbenzamide;
   N-[3-carbamoyl-5-isopropyl-thien-2-yl]3,5-dimethylbenzamide;

N-[3-carbamoyl-5-isopropyl-thien-2-yl]2-phenylpropionamide;
N-[3-carbamoyl-5-isopropyl-thien-2-yl]3-phenylpropionamide;
N-[3-carbamoyl-5-isopropyl-thien-2-yl]N-carbamyl-dl-alpha-amino-n-butyramide;
N-[3-carbamoyl-5-isopropyl-thien-2-yl]o-tolylacetamide;
N-[3-carbamoyl-5-isopropyl-thien-2-yl]m-tolylacetamide;
N-[3-carbamoyl-5-isopropyl-thien-2-yl]p-tolylacetamide;
N-[3-carbamoyl-5-isopropyl-thien-2-yl]3-pyridinepropionamide;
N-[3-carbamoyl-5-phenyl-thien-2-yl]o-anisic amide;
N-[3-carbamoyl-5-phenyl-thien-2-yl]3-methylsalicylic amide;
N-[3-carbamoyl-5-phenyl-thien-2-yl]4-methylsalicylic amide;
N-[3-carbamoyl-5-phenyl-thien-2-yl]5-methylsalicylic amide;
N-[3-carbamoyl-5-phenyl-thien-2-yl]3-methoxybenzamide;
N-[3-carbamoyl-5-phenyl-thien-2-yl]3-hydroxy-4-methylbenzamide;
N-[3-carbamoyl-5-phenyl-thien-2-yl]p-anisic amide;
N-[3-carbamoyl-5-phenyl-thien-2-yl]phenoxyacetamide;
N-[3-carbamoyl-5-phenyl-thien-2-yl]2-hydroxyphenylacetamide;
N-[3-carbamoyl-5-phenyl-thien-2-yl]3-hydroxyphenylacetamide;
N-[3-carbamoyl-5-phenyl-thien-2-yl]4-hydroxyphenylacetamide;
N-[3-carbamoyl-5-phenyl-thien-2-yl]dl-mandelic amide;
N-[3-carbamoyl-5-phenyl-thien-2-yl]3-hydroxy-o-toluic amide;
N-[3-carbamoyl-5-phenyl-thien-2-yl]alpha-fluorophenylacetamide;
N-[3-carbamoyl-5-phenyl-thien-2-y]2-fluorophenylacetamide;
N-[3-carbamoyl-5-phenyl-thien-2-yl]3-fluorophenylacetamide;
N-[3-carbamoyl-5-phenyl-thien-2-yl]4-fluorophenylacetamide;
N-[3-carbamoyl-5-phenyl-thien-2-yl]3-(2-thienyl)acrylic amide;
N-[3-carbamoyl-5-phenyl-thien-2-yl]3-(3-thienyl)-acrylic amide;
N-[3-carbamoyl-5-phenyl-thien-2-yl]3-(2-thienyl)propanoic amide;
N-[3-carbamoyl-5-phenyl-thien-2-yl]2-chlorobenzamide;
N-[3-carbamoyl-5-phenyl-thien-2-yl]3-chlorobenzamide;
N-[3-carbamoyl-5-phenyl-thien-2-yl]4-chlorobenzamide;
N-[3-carbamoyl-5-phenyl-thien-2-yl]N-propylmaleamic amide;
N-[3-carbamoyl-5-phenyl-thien-2-yl]N'-acetyl-dl-allylglycinamide;
N-[3-carbamoyl-5-phenyl-thien-2-yl]N'-acetyl-dl-prolinamide;
N-[3-carbamoyl-5-phenyl-thien-2-yl]3-(1-piperidine)propionamide;
N-[3-carbamoyl-5-phenyl-thien-2-yl]2-chloronicotinic amide;
N-[3-carbamoyl-5-phenyl-thien-2-yl]6-chloronicotinic amide;
N-[3-carbamoyl-5-phenyl-thien-2-yl]N-(acetoacetyl)glycinamide;
N-[3-carbamoyl-5-phenyl-thien-2-yl]N'-acetyl-dl-valinamide;
N-[3-carbamoyl-5-phenyl-thien-2-yl]dl-alanyl-dl-alanine;
N-[3-carbamoyl-5-phenyl-thien-2-yl]indole-6-carboxamide;
N-[3-carbamoyl-5-phenyl-thien-2-yl]benzofuran-2-carboxamide;
N-[3-carbamoyl-5-phenyl-thien-2-yl]1-phenyl-1-cyclopropanecarboxamide;
N-[3-carbamoyl-5-phenyl-thien-2-yl]cycloheptylacetamide;
N-[3-carbamoyl-5-phenyl-thien-2-yl]alpha-methylcinnamic amide;
N-[3-carbamoyl-5-phenyl-thien-2-yl]2-acetylbenzamide;
N-[3-carbamoyl-5-benzyl-thien-2-yl]4-acetylbenzamide;
N-[3-carbamoyl-5-benzyl-thien-2-yl]o-coumaric amide;
N-[3-carbamoyl-5-benzyl-thien-2-yl]3-hydroxycinnamic amide;
N-[3-carbamoyl-5-benzyl-thien-2-yl]4-hydroxycinnamic amide;
N-[3-carbamoyl-5-benzyl-thien-2-yl]p-coumaric amide;
N-[3-carbamoyl-5-benzyl-thien-2-yl]4-isopropylbenzamide;
N-[3-carbamoyl-5-benzyl-thien-2-yl]2-(3,5-xylyl)acetamide;
N-[3-carbamoyl-5-benzyl-thien-2-yl]phthalamic amide;
N-[3-carbamoyl-5-benzyl-thien-2-yl]N-carbamoylmaleamic amide;
N-[3-carbamoyl-5-benzyl-thien-2-yl]3-dimethylaminobenzamide;
N-[3-carbamoyl-5-benzyl-thien-2-yl]4-dimethylaminobenzamide;
N-[3-carbamoyl-5-benzyl-thien-2-yl]2-dimethylaminobenzamide;
N-[3-carbamoyl-5-benzyl-thien-2-yl]N'-carbamyl-dl-norvalinamide;
N-[3-carbamoyl-5-benzyl-thien-2-yl]piperonylic amide;
N-[3-carbamoyl-5-benzyl-thien-2-yl]N-carbamyl-dl-valine;
N-[3-carbamoyl-5-benzyl-thien-2-yl]alpha-fluorocinnamic amide;
N-[3-carbamoyl-5-benzyl-thien-2-yl]3-methoxy-4-methylbenzamide;
N-[3-carbamoyl-5-benzyl-thien-2-yl]indole-2-carboxamide;
N-[3-carbamoyl-5-benzyl-thien-2-yl]4-hydroxy-3,5-dimethylbenzamide;
N-[3-carbamoyl-5-benzyl-thien-2-yl]indole-3-carboxamide;
N-[3-carbamoyl-5-benzyl-thien-2-yl]benzyloxyacetamide;
N-[3-carbamoyl-5-benzyl-thien-2-yl]indole-5-carboxamide;
N-[3-carbamoyl-5-benzyl-thien-2-yl]4-dimethylaminobutyramide;
N-[3-carbamoyl-5-benzyl-thien-2-yl]indole-4-carboxamide;
N-[3-carbamoyl-5-benzyl-thien-2-yl]3-methoxysalicylic amide;
N-[3-carbamoyl-5-benzyl-thien-2-yl]4-methoxysalicylic amide;
N-[3-carbamoyl-5-benzyl-thien-2-yl]5-methoxysalicylic amide;
N-[3-carbamoyl-5-benzyl-thien-2-yl]5-benzimidazolecarboxamide;
N-[3-carbamoyl-5-benzyl-thien-2-yl]3-hydroxy-4-methoxybenzamide;
N-[3-carbamoyl-5-benzyl-thien-2-yl]indazole-3-carboxamide;
N-[3-carbamoyl-5-benzyl-thien-2-yl]vanillic amide;
N-[3-carbamoyl-5-benzyl-thien-2-yl]4-hydroxyphenoxyacetamide;
N-[3-carbamoyl-5-benzyl-thien-2-yl]6-methoxysalicylic amide;
N-[3-carbamoyl-5-benzyl-thien-2-yl]4-imidazoleacetamide;
N-[3-carbamoyl-5-benzyl-thien-2-yl]N-(2-furoyl)glycinamide;
N-[3-carbamoyl-5-benzyl-thien-2-yl]6-carboxypurine;
N-[3-carbamoyl-5-benzyl-thien-2-yl]beta-maleimidopropionamide;

N-[3-carbamoyl-5-benzyl-thien-2-yl]3,4-dihydro-2,2-dimethyl-4-oxo-2h-pyran-6-carboxamide;
N-[3-carbamoyl-5-(1-phenylethyl)-thien-2-yl]1-acetylpiperidine-4-carboxamide;
N-[3-carbamoyl-5-(1-phenylethyl)-thien-2-yl]1-naphthoic amide;
N-[3-carbamoyl-5-(1-phenylethyl)-thien-2-yl]2-naphthoic amide;
N-[3-carbamoyl-5-(1-phenylethyl)-thien-2-yl]4-chlorosalicylic amide;
N-[3-carbamoyl-5-(1-phenylethyl)-thien-2-yl]5-chlorosalicylic amide;
N-[3-carbamoyl-5-(1-phenylethyl)-thien-2-yl]3-chloro-4-hydroxybenzamide;
N-[3-carbamoyl-5-(1-phenylethyl)-thien-2-yl]3-chlorosalicylic amide;
N-[3-carbamoyl-5-(1-phenylethyl)-thien-2-yl]N'-acetyl-hydroxyproline;
N-[3-carbamoyl-5-(1-phenylethyl)-thien-2-yl]quinaldic amide;
N-[3-carbamoyl-5-(1-phenylethyl)-thien-2-yl]quinoline-3-carboxamide;
N-[3-carbamoyl-5-(1-phenylethyl)-thien-2-yl]quinoline-4-carboxamide;
N-[3-carbamoyl-5-(1-phenylethyl)-thien-2-yl]1-isoquinolinecarboxamide;
N-[3-carbamoyl-5-(1-phenylethyl)-thien-2-yl]quinoline-6-carboxamide;
N-[3-carbamoyl-5-(1-phenylethyl)-thien-2-yl]quinoline-8-carboxamide;
N-[3-carbamoyl-5-(1-phenylethyl)-thien-2-yl]6-acetamidohexanoic amide;
N-[3-carbamoyl-5-(1-phenylethyl)-thien-2-yl]N'-acetyl-dl-leucinamide;
N-[3-carbamoyl-5-(1-phenylethyl)-thien-2-yl]N',N'-di-n-propyl-1-alaninamide;
N-[3-carbamoyl-5-(1-phenylethyl)-thien-2-yl]N'-alpha-acetyl-1-asparaginamide;
N-[3-carbamoyl-5-(1-phenylethyl)-thien-2-yl]cinnoline-4-carboxamide;
N-[3-carbamoyl-5-(1-phenylethyl)-thien-2-yl]2-quinoxalinecarboxamide;
N-[3-carbamoyl-5-(1-phenylethyl)-thien-2-yl]3-methylindene-2-carboxamide;
N-[3-carbamoyl-5-(1-phenylethyl)-thien-2-yl]1-methylindole-2-carboxamide;
N-[3-carbamoyl-5-(1-phenylethyl)-thien-2-yl]1-methylindole-3-carboxamide;
N-[3-carbamoyl-5-(1-phenylethyl)-thien-2-yl]indazolone-4-carboxamide;
N-[3-carbamoyl-5-(1-phenylethyl)-thien-2-yl]3-oxo-1-indancarboxamide;
N-[3-carbamoyl-5-(1-phenylethyl)-thien-2-yl]1,2,3,4-tetrahydro-2-naphthoic amide;
N-[3-carbamoyl-5-(1-phenylethyl)-thien-2-yl]2-indanylacetamide;
N-[3-carbamoyl-5-(1-phenylethyl)-thien-2-yl]-methyl-4-imidazole-acetamide;
N-[3-carbamoyl-5-(1-phenylethyl)-thien-2-yl]arecaidinamide;
N-[3-carbamoyl-5-(1-phenylethyl)-thien-2-yl]3-benzoylpropionamide;
N-[3-carbamoyl-5-(1-phenylethyl)-thien-2-yl]4-methoxycinnamic amide;
N-[3-carbamoyl-5-(1-phenylethyl)-thien-2-yl]2-methoxycinnamic amide;
N-[3-carbamoyl-5-(1-phenylethyl)-thien-2-yl]benzo[b]thiophene-2-carboxamide;
N-[3-carbamoyl-5-(1-phenylethyl)-thien-2-yl]2-isopropyl-2-phenylacetamide;
N-[3-carbamoyl-5-(1-phenylethyl)-thien-2-yl]N'-acetylanthranilic amide;
N-[3-carbamoyl-5-(1-phenylethyl)-thien-2-yl]4-acetamidobenzamide;
N-[3-carbamoyl-5-(1-phenylethyl)-thien-2-yl]hippuric amide;
N-[3-carbamoyl-5-(1-phenylethyl)-thien-2-yl]3-acetamidobenzamide;
N-[3-carbamoyl-4,5-dimethyl-thien-2-yl]3,4-methylenedioxyphenylacetamide;
N-[3-carbamoyl-4,5-dimethyl-thien-2-yl]nicotinuric amide;
N-[3-carbamoyl-4,5-dimethyl-thien-2-yl]4-isopropoxybenzamide;
N-[3-carbamoyl-4,5-dimethyl-thien-2-yl]3-(diethylamino)propionamide;
N-[3-carbamoyl-4,5-dimethyl-thien-2-yl]2,5-dimethoxybenzamide;
N-[3-carbamoyl-4,5-dimethyl-thien-2-yl]2,6-dimethoxybenzamide;
N-[3-carbamoyl-4,5-dimethyl-thien-2-yl]3,4-dimethoxybenzamide;
N-[3-carbamoyl-4,5-dimethyl-thien-2-yl]3,5-dimethoxybenzamide;
N-[3-carbamoyl-4,5-dimethyl-thien-2-yl]2-methoxyphenoxyacetamide;
N-[3-carbamoyl-4,5-dimethyl-thien-2-yl]1-thymineacetamide;
N-[3-carbamoyl-4,5-dimethyl-thien-2-yl]indole-3-acetamide;
N-[3-carbamoyl-4,5-dimethyl-thien-2-yl]3-(2-thenoyl)-propionamide;
N-[3-carbamoyl-4,5-dimethyl-thien-2-yl]3-chloro-4-methoxybenzamide;
N-[3-carbamoyl-4,5-dimethyl-thien-2-yl]5-methylindole-2-carboxamide;
N-[3-carbamoyl-4,5-dimethyl-thien-2-yl]5-chloro-2-methoxybenzamide;
N-[3-carbamoyl-4,5-dimethyl-thien-2-yl]1-(2-carboxyphenyl)pyrrole;
N-[3-carbamoyl-4,5-dimethyl-thien-2-yl]4-(1-H-pyrrol-1-yl)benzamide;
N-[3-carbamoyl-4,5-dimethyl-thien-2-yl]1-methyl-3-indoleacetamide;
N-[3-carbamoyl-4,5-dimethyl-thien-2-yl]2-methyl-1h-benzimidazole-5-carboxamide;
N-[3-carbamoyl-4,5-dimethyl-thien-2-yl]2-(trifluoromethyl)benzamide;
N-[3-carbamoyl-4,5-dimethyl-thien-2-yl]3-(trifluoromethyl)benzamide;
N-[3-carbamoyl-4,5-dimethyl-thien-2-yl]4-(trifluoromethyl)benzamide;
N-[3-carbamoyl-4,5-dimethyl-thien-2-yl]chromone-2-carboxamide;
N-[3-carbamoyl-4,5-dimethyl-thien-2-yl]5-hydroxyindole-2-carboxamide;
N-[3-carbamoyl-4,5-dimethyl-thien-2-yl]chromone-3-carboxamide;
N-[3-carbamoyl-4,5-dimethyl-thien-2-yl]3-hydroxy-2-quinoxalinecarboxamide;
N-[3-carbamoyl-4,5-dimethyl-thien-2-yl]1-phenyl-1-cyclopentanecarboxamide;
N-[3-carbamoyl-4,5-dimethyl-thien-2-yl]2,3-dichlorobenzamide;
N-[3-carbamoyl-4,5-dimethyl-thien-2-yl]2,4-dichlorobenzamide;

N-[3-carbamoyl-4,5-dimethyl-thien-2-yl]2,5-dichlorobenzamide;
N-[3-carbamoyl-4,5-dimethyl-thien-2-yl]2,6-dichlorobenzamide;
N-[3-carbamoyl-4,5-dimethyl-thien-2-yl]3,4-dichlorobenzamide;
N-[3-carbamoyl-4,5-dimethyl-thien-2-yl]3,5-dichlorobenzamide;
N-[3-carbamoyl-4,5-dimethyl-thien-2-yl]4-oxophenylamino-2-butenoic amide;
N-[3-carbamoyl-4,5-dimethyl-thien-2-yl]4-(dimethylamino)cinnamic amide;
N-[3-carbamoyl-4,5-dimethyl-thien-2-yl]N'-chloroacetyl-dl-2-amino-n-butyramide;
N-[3-carbamoyl-4,5-dimethyl-thien-2-yl]3,4-methylenedioxycinnamic amide;
N-[3-carbamoyl-4,5-dimethyl-thien-2-yl]7-methoxybenzofuran-2-carboxamide;
N-[3-carbamoyl-4,5-dimethyl-thien-2-yl]4-benzoylbutyramide;
N-[3-carbamoyl-4-methyl-thien-2-yl]benzo[b]thiophene-3-acetamide;
N-[3-carbamoyl-4-methyl-thien-2-yl]N'-benzoyl-beta-alaninamide;
N-[3-carbamoyl-4-methyl-thien-2-yl]N'-acetyl-dl-phenylglycinamide;
N-[3-carbamoyl-4-methyl-thien-2-yl]N'-benzoyl-dl-alaninamide;
N-[3-carbamoyl-4-methyl-thien-2-yl]N'-methylhippuric amide;
N-[3-carbamoyl-4-methyl-thien-2-yl]o-hydroxyhippuric amide;
N-[3-carbamoyl-4-methyl-thien-2-yl]N'-(furan-2-yl-acryl)-glycinamide;
N-[3-carbamoyl-4-methyl-thien-2-yl](3,5-dimethoxyphenyl)acetamide;
N-[3-carbamoyl-4-methyl-thien-2-yl]3,5-dimethoxy-4-methylbenzamide;
N-[3-carbamoyl-4-methyl-thien-2-yl](2,4-dimethoxyphenyl)-acetamide;
N-[3-carbamoyl-4-methyl-thien-2-yl]5-(2-thienoyl) butyramide;
N-[3-carbamoyl-4-methyl-thien-2-yl]4-(methylsulfonyl)benzamide;
N-[3-carbamoyl-4-methyl-thien-2-yl]phenylsulphonylacetamide;
N-[3-carbamoyl-4-methyl-thien-2-yl]3-indolepropionamide;
N-[3-carbamoyl-4-methyl-thien-2-yl]3-(methylsulfonyl)benzamide;
N-[3-carbamoyl-4-methyl-thien-2-yl]2-methyl-3-indoleacetamide;
N-[3-carbamoyl-4-methyl-thien-2-yl]2-(methylsulfonyl)benzamide;
N-[3-carbamoyl-4-methyl-thien-2-yl]4-sulfonamidobenzamide;
N-[3-carbamoyl-4-methyl-thien-2-yl]5-methyl-1-phenylpyrazole-4-carboxamide;
N-[3-carbamoyl-4-methyl-thien-2-yl]5-methyl-3-phenylisoxazole-4-carboxamide;
N-[3-carbamoyl-4-methyl-thien-2-yl]2-hydroxy-5-(1h-pyrrol-1-yl)benzamide;
N-[3-carbamoyl-4-methyl-thien-2-yl]4-methyl-2-phenyl-1,2,3-triazole-5-carboxamide;
N-[3-carbamoyl-4-methyl-thien-2-yl]N'-acetyl-dl-phenylglycinamide;
N-[3-carbamoyl-4-methyl-thien-2-yl]2,3-dimethoxycinnamic amide;
N-[3-carbamoyl-4-methyl-thien-2-yl]2-benzimidazolepropionamide;
N-[3-carbamoyl-4-methyl-thien-2-yl]2,5-dimethoxycinnamic amide;
N-[3-carbamoyl-4-methyl-thien-2-yl]3,4-dimethoxycinnamic amide;
N-[3-carbamoyl-4-methyl-thien-2-yl]3,5-dimethoxycinnamic amide;
N-[3-carbamoyl-4-methyl-thien-2-yl]2,4-dimethoxycinnamic amide;
N-[3-carbamoyl-4-methyl-thien-2-yl]3-(3,4-dimethoxyphenyl)propionamide;
N-[3-carbamoyl-4-methyl-thien-2-yl]9-fluorenecarboxamide;
N-[3-carbamoyl-4-methyl-thien-2-yl]6-chloro(2H)-1-benzopyran-3-carboxamide;
N-[3-carbamoyl-4-methyl-thien-2-yl]epsilon-maleimidocaproic amide;
N-[3-carbamoyl-4-methyl-thien-2-yl]5-methoxyindole-2-carboxamide;
N-[3-carbamoyl-4-methyl-thien-2-yl]2,3,4-trimethoxybenzamide;
N-[3-carbamoyl-4-methyl-thien-2-yl]5-hydroxyindole-3-acetamide;
N-[3-carbamoyl-4-methyl-thien-2-yl]2,4,5-trimethoxybenzamide;

or a pharmaceutically acceptable salt thereof.

6. A 3-aminocarbonyl-2-carboxamido-thiophene compound having the formula (I):

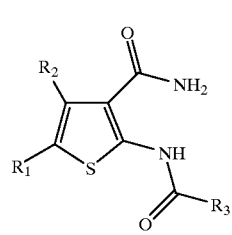

wherein:
$R_1$ and $R_2$ are, independently from each other, hydrogen, halogen or an optionally substituted group comprising aryl, straight or branched $C_1$–$C_6$ alkyl or aryl $C_1$–$C_6$ alkyl;
$R_3$ is an optionally substituted group comprising:
i) straight or branched $C_1$–$C_8$ alkyl, which is substituted, $C_2$–$C_6$ alkenyl, $C_2$–$C_6$ alkynyl or $C_2$–$C_6$ alkylcarbonyl;
ii) aryl;
iii) 3 to 7 membered carbocycle; or
iv) 5 to 7 membered heterocycle with from 1 to 3 heteroatoms of nitrogen, oxygen or sulphur;
or a pharmaceutically acceptable salt thereof, provided that:
a) when $R_1$ is phenyl and $R_2$ is hydrogen, $R_3$ is other than phenyl or methyl; and
b) when $R_1$ and $R_2$ are both methyl, $R_3$ is other than p-methoxyphenyl;
wherein said straight or branched $C_1$–$C_8$ alkyl is substituted by one or more groups comprising halogen, nitro, oxo, carboxy, cyano, alkyl, perfluorinated alkyl, alkenyl, alkynyl, cycloalkyl, aryl, amino, alkylamino, arylamino, ureido, alkylureido, carbonylamino, alkylcarboxylamino, hydroxy, alkoxy, alkylthio, alkylsulfonyl, or aminosulfonyl.

7. A 3-aminocarbonyl-2-carboxamido-thiophene compound having the formula (I):

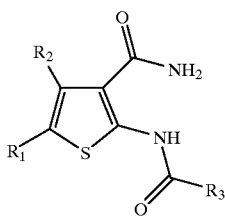

(I)

wherein:

R$_1$ and R$_2$ are, independently from each other, hydrogen, halogen or an optionally substituted group comprising aryl, straight or branched C$_1$–C$_6$ alkyl or aryl C$_1$–C$_6$ alkyl;

R$_3$ is an optionally substituted group comprising:
  i) C$_2$–C$_6$ alkenyl, C$_2$–C$_6$ alkynyl or C$_2$–C$_6$ alkylcarbonyl;
  ii) aryl;
  iii) 3 to 7 membered carbocycle; or
  iv) 5 to 7 membered heterocycle with from 1 to 3 heteroatoms selected from nitrogen, oxygen and sulphur;

or a pharmaceutically acceptable salt thereof, provided that:

a) when R$_1$ is phenyl and R$_2$ is hydrogen, R$_3$ is other than phenyl or methyl; and
  b) when R$_1$ and R$_2$ are both methyl, R$_3$ is other than p-methoxyphenyl.

8. The compound of claim 1 R$_1$ and R$_2$ together form a —(CH$_2$)$_m$—(NR$_4$)$_n$—(CH$_2$)$_p$— group, n is 0 or 1, R$_4$ if present is C$_1$–C$_4$ alkyl, m+n+p is 4 and R$_3$ is as defined in claim 1.

9. The compound of claim 1 wherein R$_1$ and R$_2$ are both methyl groups or form, together, a —(CH$_2$)$_4$— group or a —CH$_2$—NR$_4$—(CH$_2$)$_2$— group wherein R$_4$ is C$_1$–C$_4$ alkyl, and R$_3$ is as defined in claim 1.

10. Any specific 3-aminocarbonyl-2-carboxamido-thiophene of claim 1 which is obtainable through a process comprising reacting the 2-amino-thiophene derivative of formula (II)

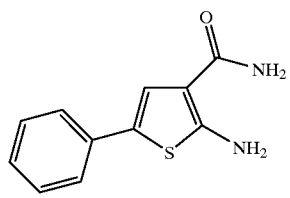

(II)

with each one of the carboxylic acids listed in table II other than benzoic or acetic acid.

11. Any specific 3-aminocarbonyl-2-carboxamido-thiophene of claim 1 which is obtainable through a process comprising reacting the 2-amino-thiophene derivative of formula (II)

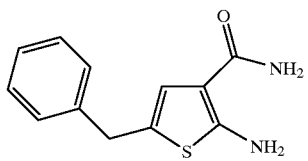

(II)

with each one of the carboxylic acids of table II.

12. Any specific 3-aminocarbonyl-2-carboxamido-thiophene of claim 1 which is obtainable through a process comprising reacting the 2-amino-thiophene derivative of formula (II)

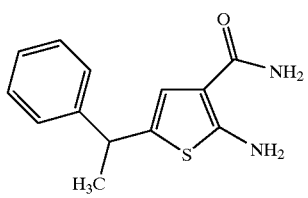

(III)

with each one of the carboxylic acids of table II.

13. Any specific 3-aminocarbonyl-2-carboxamido-thiophene of claim 1 which is obtainable through a process comprising reacting the 2-amino-thiophene derivative of formula (II)

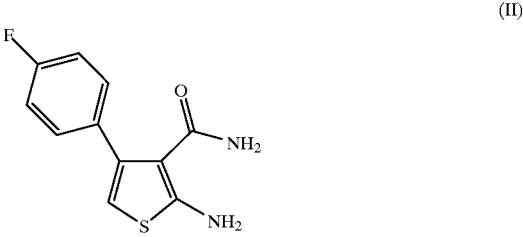

(II)

with each one of the carboxylic acids of table II.

14. Any specific 3-aminocarbonyl-2-carboxamido-thiophene of claim 1 which is obtainable through a process comprising reacting the 2-amino-thiophene derivative of formula (II)

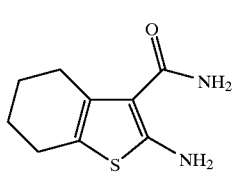

(II)

with each one of the carboxylic acids of table II provided that R$_3$ is other than methyl, ethyl, dimethylaminomethyl, diethylaminoethyl, phenyl, 4-chlorophenyl, 4-methoxyphenyl or 2-(N-piperidino)ethyl.

15. Any specific 3-aminocarbonyl-2-carboxamido-thiophene of claim 1 which is obtainable through a process comprising reacting the 2-amino-thiophene derivative of formula (II)

with each one of the carboxylic acids of table II other than acetic.

16. The compound of claim 6, wherein $R_1$ and $R_2$ are, each independently, hydrogen, $C_1$–$C_4$ alkyl or optionally substituted aryl or aryl $C_1$–$C_4$ aryl.

17. The compound of claim 6, wherein $R_1$ is selected from the group consisting of isopropyl, phenyl, phenylmethyl and 1-phenylethyl; and $R_2$ is hydrogen.

18. The compound of claim 6, wherein $R_1$ is hydrogen; and $R_2$ is selected from the group consisting of methyl and 4-fluorophenyl.

19. The compound of claim 7, wherein $R_1$ and $R_2$ are each independently, hydrogen, $C_1$–$C_4$ alkyl or optionally substituted aryl or aryl $C_1$–$C_4$ aryl.

20. The compound of claim 7, wherein $R_1$ is selected from the group consisting of isopropyl, phenyl, phenylmethyl and 1-phenylethyl; and $R_2$ is hydrogen.

21. The compound of claim 7, wherein $R_1$ is hydrogen; and $R_2$ is selected from the group consisting of methyl and 4-fluorophenyl.

22. A process of preparing a thiophene compound of claim 1, where $R_1$ is isopropyl, and $R_2$ is hydrogen, which comprises reacting a 2-amino-thiophene compound of the formula:

with a carboxylic acid of the formula $R_3COOH$, wherein $R_3$ is as defined in Table II of the specification.

23. A process for preparing a thiophene compound of claim 1, where each of $R_1$ and $R_2$ is methyl, which comprises reacting a 2-amino-thiophene compound of the formula:

with a carboxylic acid of the formula $R_3COOH$, wherein $R_3$ is as defined in Table II of the specification, with the proviso that p-anisic acid is not included as the carboxylic acid.

24. A process for preparing a thiophene compound of claim 1, where $R_1$ is hydrogen and $R_2$ is methyl, which comprises reacting a 2-amino-thiophene compound of the formula (II):

with a carboxylic acid of the formula $R_3COOH$, wherein $R_3$ is as defined in Table II of the specification.

25. A process for preparing the 3-aminocarbonyl-2-carboxamido-thiophene of claim 1 of the formula (I), or a pharmaceutically acceptable salt thereof, which process comprises reacting a compound of formula (II):

(II)

wherein $R_1$ and $R_2$ are defined in claim 1, with a compound of formula (III)

$$R_3\text{—COX} \qquad (III)$$

wherein $R_3$ is as defined in claim 1, and X is hydroxy or a suitable leaving group; and, optionally converting the 2-aminocarbonyl-3-carboxamido-thiophene compound of the of formula (I) into the salt thereof.

26. The process of claim 25, wherein the X leaving group of formula (III) is a halogen atom.

27. The process of claim 25, wherein X is hydroxy, chlorine or bromine.

28. A pharmaceutical composition, which comprises one or more compounds of claim 1, and a pharmaceutically acceptable carrier.

29. A pharmaceutical composition, which comprises one or more compounds of claim 6, and a pharmaceutically acceptable carrier.

30. A pharmaceutical composition, which comprises one or more compounds of claim 7, and a pharmaceutically acceptable carrier.

31. A method for treating diseases associated with an altered protein kinase activity which comprises administering to a mammal in need thereof an effective amount of a 3-aminocarbonyl-2-carboxamido-thiophene derivative represented by formula (I):

(I)

wherein
$R_1$ and $R_2$ are, independently from each other, hydrogen, halogen or an optionally substituted group selected from aryl, straight or branched $C_1$–$C_6$ alkyl or aryl $C_1$–$C_6$ alkyl;

or, taken together with the thiophene bond to which they are linked, $R_1$ and $R_2$ form a —$(CH_2)_m$—$(NR_4)_n$—$(CH_2)_p$— group wherein m and p are, each independently, an integer form 1 to 3, n is 0 or 1 and m+n+p is an integer from 3 to 5; and $R_4$ is hydrogen or an optionally substituted straight or branched $C_1$–$C_6$ alkyl group;

$R_3$ is a group, optionally further substituted, selected from:
  i) straight or branched $C_1$–$C_8$ alkyl, $C_2$–$C_6$ alkenyl, $C_2$–$C_6$ alkynyl or $C_2$–$C_6$ alkylcarbonyl;
  ii) aryl;
  iii) 3 to 7 membered carbocycle;
  iv) 5 to 7 membered heterocycle with from 1 to 3 heteroatoms selected from nitrogen, oxygen and sulphur;

or a pharmaceutically acceptable salt thereof.

32. The method of claim 31 wherein the disease associated with an altered protein kinase activity is a cell proliferative disorder selected from the group consisting of cancer, Alzheimer's disease, viral infections, auto-immune diseases and neurodegenerative disordes.

33. The method of claim 32 wherein the cancer is selected from carcinoma, squamous cell carcinoma, hematopoietic tumors of lymphoid or myeloid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

34. The method of claim 31 wherein the cell proliferative disorder is selected from benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

35. The method of claim 31 which provides tumor angiogenesis and metastasis inhibition.

36. The method of claim 31 further comprising subjecting the mammal in need thereof to a radiation therapy or chemotherapy regimen in combination with at least one cytostatic or cytotoxic agent.

37. The method of claim 31 wherein the mammal in need thereof is a human.

38. The method of claim 31 wherein $R_1$ and $R_2$ are selected, each independently, from hydrogen, $C_1$–$C_4$ alkyl or optionally substituted aryl or aryl $C_1$–$C_4$ alkyl groups and $R_3$ is as defined in claim 1.

39. The method of claim 31 wherein $R_1$ and $R_2$ together form a —$(CH_2)_m$—$(NR_4)_n$—$(CH_2)_p$— group, n is 0 or 1, $R_4$ if present is $C_1$–$C_4$ alkyl, m+n+p is 4 and $R_3$ is as defined in claim 1.

40. The method of claim 31 wherein $R_1$ is selected from isopropyl, phenyl, phenylmethyl or 1-phenylethyl, $R_2$ is hydrogen and $R_3$ is as defined in claim 1.

41. The method of claim 31 wherein $R_1$ is hydrogen, $R_2$ is methyl or 4-fluorophenyl and $R_3$ is as defined in claim 1.

42. The method of claim 31 wherein $R_1$ and $R_2$ are both methyl groups or form, together, a —$(CH_2)_4$— group or a —$CH_2$—$NR_4$—$(CH_2)_2$— group wherein $R_4$ is $C_1$–$C_4$ alkyl, and $R_3$ is as defined in claim 1.

43. A method of treating a mammalian disease by inhibition of protein kinases, which comprises administering an effective amount of one or more compounds of claim 1, to a mammal in need thereof.

44. A method of treating a mammalian disease by inhibition of protein kinases, which comprises administering an effective amount of one or more compounds of claim 6, to a mammal in need thereof.

45. A method of treating a mammalian disease by inhibition of protein kinases, which comprises administering an effective amount of one or more compounds of claim 7, to a mammal in need thereof.

* * * * *

UNITED STATES PATENT AND TRADEMARK OFFICE
CERTIFICATE OF CORRECTION

PATENT NO. : 6,414,013 B1
DATED : July 2, 2002
INVENTOR(S) : Fancelli et al.

It is certified that error appears in the above-identified patent and that said Letters Patent is hereby corrected as shown below:

Title page, Item [54] and Column 1, lines 1-5,
Title should read: -- [54] THIOPHENE COMPOUNDS, PROCESS FOR PREPARING THE SAME, AND PHARMACEUTICAL COMPOSITIONS CONTAINING THE SAME --

Signed and Sealed this

Thirty-first Day of December, 2002

JAMES E. ROGAN
*Director of the United States Patent and Trademark Office*